United States Patent
Gerber et al.

(10) Patent No.: US 10,448,889 B2
(45) Date of Patent: Oct. 22, 2019

(54) DETERMINING NERVE LOCATION RELATIVE TO ELECTRODES

(75) Inventors: Martin T. Gerber, Maple Grove, MN (US); Steven M. Goetz, North Oaks, MN (US); Christopher Poletto, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 308 days.

(21) Appl. No.: 13/456,829

(22) Filed: Apr. 26, 2012

(65) Prior Publication Data

US 2012/0277621 A1    Nov. 1, 2012

Related U.S. Application Data

(60) Provisional application No. 61/480,916, filed on Apr. 29, 2011, provisional application No. 61/480,864, filed on Apr. 29, 2011, provisional application No. 61/480,887, filed on Apr. 29, 2011, provisional application No. 61/480,928, filed on Apr. 29, 2011, (Continued)

(51) Int. Cl.
| | |
|---|---|
| *A61B 5/00* | (2006.01) |
| *A61N 1/36* | (2006.01) |
| *A61N 1/372* | (2006.01) |
| *A61N 1/05* | (2006.01) |

(52) U.S. Cl.
CPC .......... *A61B 5/4893* (2013.01); *A61B 5/0031* (2013.01); *A61B 5/4058* (2013.01); *A61B 5/4836* (2013.01); *A61B 5/686* (2013.01); *A61B 5/6868* (2013.01); *A61B 5/6877* (2013.01); *A61N 1/36128* (2013.01); *A61N 1/37247* (2013.01); *A61N 1/0529* (2013.01); *A61N 1/0551* (2013.01); *A61N 1/36185* (2013.01)

(58) Field of Classification Search
CPC ............ A61N 1/36185; A61N 1/37247; A61B 5/6877
USPC ........................................................ 600/554
See application file for complete search history.

(56) References Cited

U.S. PATENT DOCUMENTS

| | | |
|---|---|---|
| 5,306,292 A | 4/1994 | Lindegren |
| 5,626,629 A | 5/1997 | Faltys et al. |
| | (Continued) | |

FOREIGN PATENT DOCUMENTS

| | | | | |
|---|---|---|---|---|
| EP | 1181951 B1 | 3/2004 | | |
| WO | WO 2004064634 A1 * | 8/2004 | ........... | A61B 5/0488 |
| | (Continued) | | | |

OTHER PUBLICATIONS

U.S. Appl. No. 13/457,063, filed Apr. 26, 2012, entitled "Electrical Stimulation Therapy Based on Head Position."

(Continued)

*Primary Examiner* — Patrick Fernandes
(74) *Attorney, Agent, or Firm* — Shumaker & Sieffert, P.A.

(57) ABSTRACT

An implantable nerve stimulator is implanted in a patient near a nerve target. The implantable nerve stimulator has a plurality of electrodes through which stimulation is provided to the nerve target. The relative location of the nerve target and the electrodes may be determined by applying stimulation to the nerves via each of the electrodes, determining an effect of the stimulation for each of the electrodes, and mapping a location of the nerve relative to the electrodes based on the effect of the stimulation for each of the electrodes.

27 Claims, 17 Drawing Sheets

Related U.S. Application Data provisional application No. 61/488,007, filed on May 19, 2011.

(56) References Cited

U.S. PATENT DOCUMENTS

| | | | |
|---|---|---|---|
| 5,775,331 A * | 7/1998 | Raymond | A61N 1/05 600/554 |
| 5,928,272 A | 7/1999 | Adkins et al. | |
| 6,259,945 B1 * | 7/2001 | Epstein et al. | 600/547 |
| 6,393,325 B1 | 5/2002 | Mann et al. | |
| 6,473,644 B1 | 10/2002 | Terry, Jr. et al. | |
| 6,587,724 B2 | 7/2003 | Mann | |
| 6,622,048 B1 * | 9/2003 | Mann | A61N 1/36071 607/46 |
| 6,640,136 B1 | 10/2003 | Helland et al. | |
| 6,731,986 B2 | 5/2004 | Mann | |
| 7,065,412 B2 * | 6/2006 | Swoyer et al. | 607/117 |
| 7,104,965 B1 | 9/2006 | Jiang et al. | |
| 7,174,215 B2 | 2/2007 | Bradley | |
| 7,254,446 B1 | 8/2007 | Erickson et al. | |
| 7,317,944 B1 | 1/2008 | Overstreet | |
| 7,317,948 B1 * | 1/2008 | King et al. | 607/62 |
| 7,499,752 B2 | 3/2009 | Machino et al. | |
| 7,519,431 B2 | 4/2009 | Goetz et al. | |
| 7,567,840 B2 | 7/2009 | Armstrong | |
| 7,578,819 B2 | 8/2009 | Bleich et al. | |
| 7,643,881 B2 | 1/2010 | Armstrong | |
| 7,689,286 B2 | 3/2010 | Pastore et al. | |
| 7,711,419 B2 | 5/2010 | Armstrong et al. | |
| 2002/0072770 A1 | 6/2002 | Pless | |
| 2003/0073899 A1 | 4/2003 | Ruohonen et al. | |
| 2003/0153959 A1 | 8/2003 | Thacker et al. | |
| 2004/0116978 A1 * | 6/2004 | Bradley | A61N 1/36071 607/48 |
| 2004/0158298 A1 * | 8/2004 | Gliner et al. | 607/48 |
| 2004/0167586 A1 | 8/2004 | Overstreet | |
| 2005/0107654 A1 | 5/2005 | Riehl | |
| 2005/0119714 A1 * | 6/2005 | Sieracki | A61N 1/08 607/48 |
| 2005/0222626 A1 | 10/2005 | DiLorenzo | |
| 2005/0245987 A1 | 11/2005 | Woods et al. | |
| 2006/0074450 A1 | 4/2006 | Boveja et al. | |
| 2006/0085048 A1 * | 4/2006 | Cory | A61B 5/0536 607/48 |
| 2006/0167498 A1 | 7/2006 | DiLorenzo | |
| 2006/0173510 A1 | 8/2006 | Besio et al. | |
| 2006/0195159 A1 * | 8/2006 | Bradley | A61N 1/36132 607/48 |
| 2006/0229677 A1 * | 10/2006 | Moffitt | A61N 1/056 607/2 |
| 2006/0253174 A1 * | 11/2006 | King | A61N 1/36185 607/62 |
| 2007/0016097 A1 | 1/2007 | Farquhar et al. | |
| 2007/0043395 A1 | 2/2007 | Wei et al. | |
| 2007/0233194 A1 | 10/2007 | Craig | |
| 2007/0255320 A1 | 11/2007 | Inman et al. | |
| 2008/0086175 A1 | 4/2008 | Libbus et al. | |
| 2008/0147140 A1 | 6/2008 | Ternes et al. | |
| 2008/0234780 A1 * | 9/2008 | Smith | A61N 1/36139 607/45 |
| 2008/0269812 A1 | 10/2008 | Gerber et al. | |
| 2008/0281381 A1 | 11/2008 | Gerber et al. | |
| 2009/0030493 A1 | 1/2009 | Colborn et al. | |
| 2009/0043352 A1 | 2/2009 | Brooke et al. | |
| 2009/0076561 A1 | 3/2009 | Libbus et al. | |
| 2009/0112281 A1 | 4/2009 | Miyazawa et al. | |
| 2009/0198294 A1 | 8/2009 | Rossing et al. | |
| 2009/0299214 A1 * | 12/2009 | Wu | A61B 5/04001 600/554 |
| 2010/0010383 A1 | 1/2010 | Skelton et al. | |
| 2010/0010390 A1 | 1/2010 | Skelton et al. | |
| 2010/0010576 A1 | 1/2010 | Skelton et al. | |
| 2010/0010580 A1 | 1/2010 | Skelton et al. | |
| 2010/0010584 A1 | 1/2010 | Skelton et al. | |
| 2010/0010585 A1 | 1/2010 | Davis et al. | |
| 2010/0010586 A1 | 1/2010 | Skelton et al. | |
| 2010/0030299 A1 | 2/2010 | Covalin | |
| 2010/0114192 A1 | 5/2010 | Jaax et al. | |
| 2010/0114204 A1 | 5/2010 | Burnes et al. | |
| 2010/0114221 A1 | 5/2010 | Krause et al. | |
| 2010/0121408 A1 | 5/2010 | Imran et al. | |
| 2010/0161007 A1 | 6/2010 | King | |
| 2010/0249875 A1 | 9/2010 | Kishawi et al. | |
| 2010/0262209 A1 * | 10/2010 | King et al. | 607/62 |
| 2011/0046506 A1 * | 2/2011 | Durand | A61B 5/04001 600/547 |
| 2011/0270119 A1 * | 11/2011 | Rasmussen | A61B 5/4893 600/554 |
| 2011/0276107 A1 | 11/2011 | Simon et al. | |
| 2012/0109004 A1 * | 5/2012 | Cadwell | A61B 5/0488 600/554 |
| 2012/0271382 A1 | 10/2012 | Arcot-Krishnamurthy et al. | |

FOREIGN PATENT DOCUMENTS

| | | |
|---|---|---|
| WO | 2006073393 A1 | 7/2006 |
| WO | 2009134478 A1 | 11/2009 |
| WO | 2009158389 A1 | 12/2009 |
| WO | 2010065146 A1 | 6/2010 |
| WO | 2010105261 A1 | 9/2010 |

OTHER PUBLICATIONS

U.S. Appl. No. 13/456,969, filed Apr. 26, 2012, entitled "Dual Prophylactic and Abortive Electrical Stimulation."

Schachter et al., "Warning Signs of Seizures," Aug. 2013, Epilepsy Foundation, retrieved from internet www.epilepsy.com/get-help/managing-you-epilepsy/understanding-seizures-and-emergencies/warning-signs-seizures on Sep. 30, 2014, 2 pp.

Final Office Action from U.S. Appl. No. 13/457,063, dated Apr. 6, 2016, 17 pp.

Response to the Office Action dated Nov. 3, 2015, from U.S. Appl. No. 13/457,063, Response filed Feb. 3, 2016, 22 pp.

Advisory Action from U.S. Appl. No. 13/457,063, dated Jun. 28, 2016, 5 pp.

Office Action from U.S. Appl. No. 13/457,063, dated Jul. 26, 2016, 17 pp.

Response to Office Action dated Apr. 6, 2016, from U.S. Appl. No. 13/457,063, filed Jun. 3, 2016, 25 pp.

Response to Office Action dated Jul. 26, 2016, from U.S. Appl. No. 13/457,063, filed Nov. 28, 2016, 22 pp.

Notice of Allowance from U.S. Appl. No. 13/457,063, dated Jan. 6, 2017, 14 pp.

Office Action from U.S. Appl. No. 13/457,063, dated Apr. 26, 2012, 17 pp.

* cited by examiner

DETERMINING NERVE LOCATION RELATIVE TO ELECTRODES

This application claims the benefit of U.S. Provisional Application No. 61/480,916, filed on Apr. 29, 2011, U.S. Provisional Application No. 61/480,864, filed Apr. 29, 2011, U.S. Provisional Application No. 61/480,887, filed Apr. 29, 2011, U.S. Provisional Application No. 61/480,928, filed Apr. 29, 2011, and U.S. Provisional Application No. 61/488,007, filed May 19, 2011, the entire contents of each of which is incorporated herein by reference.

TECHNICAL FIELD

The invention relates to programming implantable nerve stimulators.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, migraines, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a current or voltage pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, examples according to this disclosure employ techniques for efficiently determining one or more thresholds for each of a number of implanted electrodes as a baseline for programming and delivering efficacious stimulation therapy to a patient via the electrodes. The disclosed examples also leverage the stimulation thresholds in the course of applying several techniques that may improve the method by which therapy is programmed, as well as the effectiveness of the therapy ultimately delivered based on such programming. For example, stimulation thresholds may be employed to cluster multiple individual electrodes or electrode combinations into a single stimulation program defining delivery of stimulation therapy to increase utilization of resources that may provide efficacious results to a patient. In another example, stimulation thresholds may be used to map the relative locations of target nerves and the electrodes.

In one example, a method includes applying stimulation to a nerve via each of a plurality of implantable electrodes arranged proximate to the nerve, determining an effect of the stimulation for each of the electrodes, and mapping a location of the nerve relative to the electrodes based on the effect of the stimulation for each of the electrodes In another example, a system includes an implantable electrical stimulator connected to a plurality of electrodes, and a processor configured to control the electrical stimulator to apply stimulation to a nerve via each of a plurality of implantable electrodes arranged proximate to the nerve, determine an effect of the stimulation for each of the electrodes, and map a location of the nerve relative to the electrodes based on the effect of the stimulation for each of the electrodes.

In another example, a computer-readable storage medium including instruction for causing a programmable processor to apply stimulation to a nerve via each of a plurality of implantable electrodes arranged proximate to the nerve, determine an effect of the stimulation for each of the electrodes, and map a location of the nerve relative to the electrodes based on the effect of the stimulation of each of the electrodes.

DETAILED DESCRIPTION

Figure 1A:
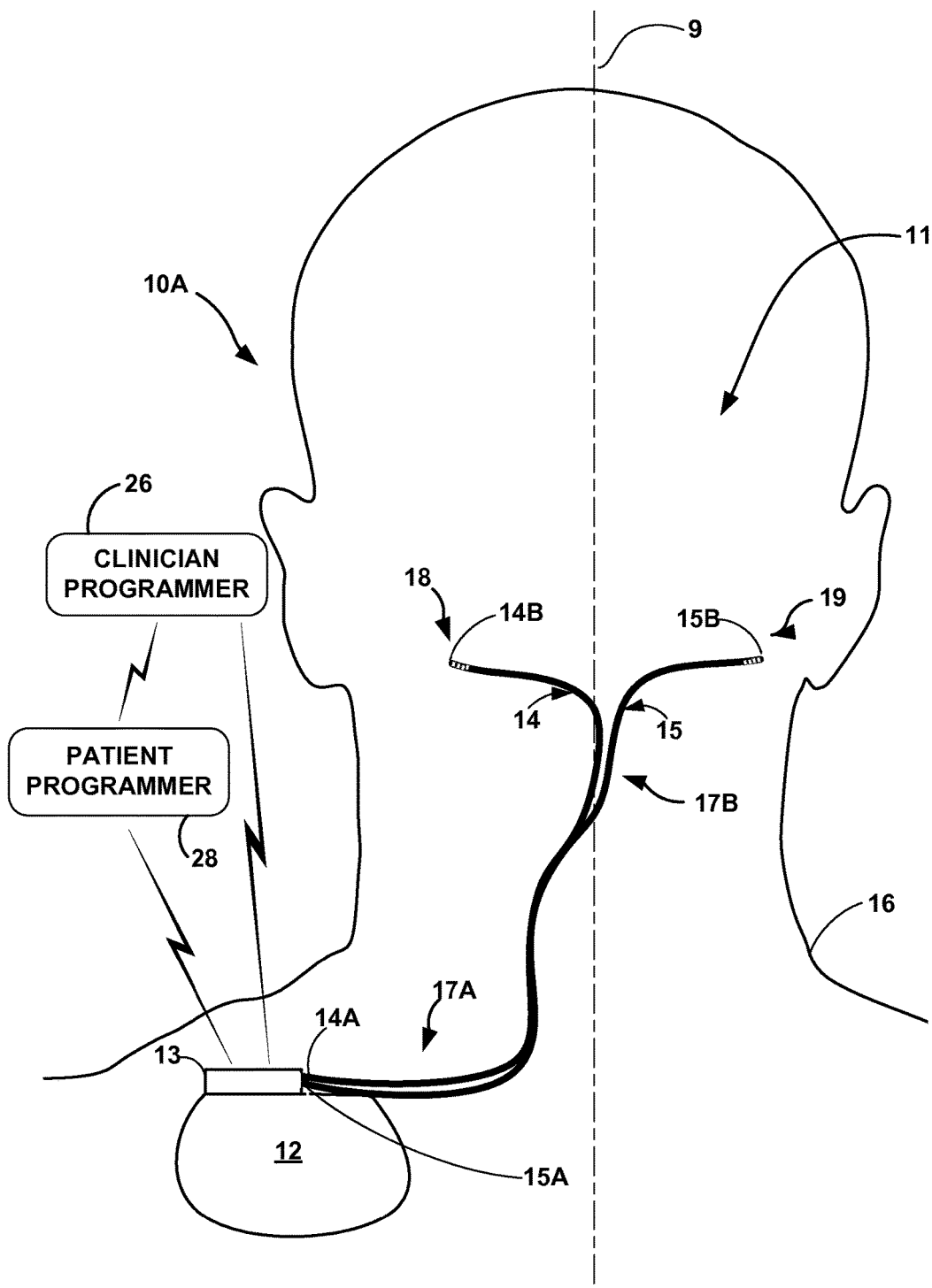
FIGS. 1A and 1B are conceptual diagrams illustrating example therapy systems that include an implantable electrical stimulator coupled to an implantable stimulation lead.

Implantable medical devices (IMDs), including, e.g., electrical stimulation devices, commonly include the actual implantable device, including, e.g., a housing containing a battery, device circuitry, and a pulse generator, and a therapy delivery component, e.g., a stimulation lead carrying one or more electrodes by which therapy is delivered to a point of interest within a patient. After an IMD and an associated lead or leads have been implanted within a patient, the IMD may be programmed before the patient begins receiving chronic stimulation therapy for one or more conditions for which the device has been implanted. Programming electrical stimulation therapy generally includes testing stimulation configured according to different electrode combinations and stimulation parameters to determine which electrodes and parameter values deliver the most efficacious therapy to a particular patient.

As used in this disclosure, electrode combination may refer to any number of electrode(s) by which stimulation is delivered to a patient, including monopolar, bipolar, multipolar, and unipolar electrode combinations. In some examples, stimulation is described as delivered by one electrode adjacent to a target delivery site. Some such examples may refer to monopolar or unipolar electrode combinations including the electrode adjacent the target delivery site and an electrode associated with a housing of the IMD to which the electrode is connected. Multipolar or bipolar may refer to electrode combinations in which all active electrodes are near the delivery site. Example stimulation parameters by which stimulation delivered via an electrode combination may be defined include stimulation amplitude (e.g., current or voltage), pulse width, and frequency. In some cases, efficacious electrode combinations and parameters will be defined as a stimulation program by which therapy may be delivered to the patient after the programming session is concluded. A programming session may yield multiple efficacious stimulation programs, which may remain separate or which may be grouped together in one or more stimulation program groups.

One aspect of programming an IMD, is determining the acceptable and efficacious stimulation intensities at which to deliver the electrical stimulation to the patient. Stimulation intensities that are efficacious in treating symptoms of a condition, but do not produce unacceptable side effects generally vary from patient to patient, and, as such, may need to be tested for each patient receiving stimulation from an IMD. As used in this disclosure, stimulation intensity may refer to the amount of energy delivered to a patient through electrical stimulation. As such, stimulation intensity may be a function of both the amplitude, e.g., current or voltage, and the pulse width of the stimulation pulses delivered to the patient during an electrical stimulation session. Changes in stimulation intensity, i.e. increases or decreases, may therefore correspond to a change in one or both of the stimulation amplitude and the pulse width.

One method of testing stimulation intensities for a patient is to establish one or more stimulation thresholds, which may be associated with each of a number of different electrodes or different electrode combinations by which the stimulation is delivered. A stimulation threshold may refer to a level of stimulation intensity at which a patient experiences a perceivable sensation as a result of stimulation delivered at that intensity level. Example stimulation thresholds include perception, parasthesia, discomfort, muscle recruitment, and pain thresholds. Stimulation delivered to a patient may be defined by a range of stimulation intensities within which efficacious therapy is possible without unacceptable side effects. Such a range may be referred to as a usability range and may generally include a lower bound or lower stimulation threshold and an upper bound or high stimulation threshold. Example lower stimulation thresholds include the perception and parasthesia thresholds. Example high stimulation thresholds include the discomfort, muscle recruitment, and pain thresholds. Defining usability ranges for different individual electrodes or combinations of electrodes by which stimulation will be delivered to the patient may assist in programming by narrowing the range of possible stimulation intensities that may produce efficacious stimulation therapy to the patient. For example, by defining a usability range between a perception and a pain threshold of a patient for a particular electrode or combination of electrodes, testing within that range may result in stimulation intensities that are high enough to produce perceivable effects but not too high so as to produce undesirable side effects, such as pain.

As noted above, a stimulation threshold may refer to a level of stimulation intensity at which a patient experiences a perceivable sensation as a result of stimulation delivered at that intensity level, and different example thresholds include perception, parasthesia, discomfort, muscle recruitment, and pain thresholds. Stimulation thresholds may be determined based on patient feedback, e.g., by increasing the intensity of stimulation until the patient indicates a perceived effect of the stimulation is felt. The perception threshold for an electrode or combination of electrodes may refer to the level of stimulation intensity at which the patient first perceives the electrical stimulation. The parasthesia threshold may refer to the level of stimulation intensity at which the patient first feels a "tingling" sensation that radiates away from the stimulating electrode or is perceived to reside some distance from the stimulating electrode as a result of the stimulation. The discomfort threshold may refer to the level of intensity at which the patient feels an uncomfortable effect of the stimulation. The pain threshold may refer to the level of intensity at which the patient feels pain. Discomfort and pain may both indicate undesirable effects of the stimulation, but the character of the two effects may differ. For example, discomfort may refer to a level of blunt pressure, which, although not painful, is nevertheless uncomfortable for the patient. Discomfort may have a relatively wide range of levels at which the effect becomes increasingly intolerable to the patient. Pain, on the other hand, may refer to a sharp sensation that causes an effect that, as the level of the effect increases, is immediately, or quickly becomes, intolerable to the patient such that the range of levels at which the pain may be tolerable to the patient may be much narrower than the discomfort range. The muscle recruitment threshold may refer to the level of stimulation intensity at which one or more of the muscles in the area of a nerve of interest begin to twitch. The muscle twitching occurs based on activation of nerves leading to muscles in the area of interest as a result of the stimulation.

In some examples, each electrode on an implanted lead may be associated with at least one threshold. For example, an electrode may deliver stimulation that produces a perception threshold that also corresponds to one or more of a pain, discomfort or muscle recruitment threshold. In another example, an electrode may be associated with a number of thresholds, including, e.g., two or more of any of the perception, paresthesia, pain, discomfort and muscle recruitment thresholds.

In some examples, one or more of the stimulation threshold may be grouped as a general type of threshold. For example, the pain, discomfort and muscle recruitment thresholds may be collectively considered an upper threshold which signals a stimulation intensity above which undesirable side effects occur. Another example may be a therapeutic effect threshold. Perception, paresthesia, and any other generally positive effect-determined thresholds may be grouped together.

In addition to relating to potentially efficacious levels of stimulation intensity, the values of different stimulation thresholds, as well as usability ranges defined by more than one threshold, may also be indicative of the likelihood that the electrode or electrode combination associated with the thresholds will produce efficacious therapy. The efficacy of the electrode(s) is indicated by stimulation thresholds, at least in part, because the values of the thresholds for the electrode(s) are related to the proximity and orientation of the electrode to the target tissue at which stimulation is directed, e.g., a target nerve or a group of nerves. In other words, stimulation thresholds for an electrode may be indicative of the position of the electrode within the body of the patient relative to the target nerve, or other tissue of interest, which relative position may affect the degree to which the electrode may be used to provide effective therapy to the patient. For example, one or more of the electrodes may be too close to a nerve such that stimulation delivered via the electrodes causes discomfort at a very low stimulation intensity, which may make the usability range for the electrodes vary narrow or even practically equal to zero (e.g., where the first perceivable effect of stimulation is discomfort or pain). Conversely, in some examples, electrode(s) delivering stimulation to a target nerve may be so far away from the nerve that the implantable stimulator is unable to provide stimulation at an intensity level adequate to provide effective therapy to the patient.

The position of implanted electrodes within a patient's body relative to target nerves, or other tissue may, in some cases, be known as a result of the surgical procedure employed for the implantation. However, generally, implantation procedures that directly or indirectly map the location of electrodes relative to target stimulation sites within the body may be more complicated, take longer, and be more invasive, thereby increasing the costs and potentially the risks of such procedures. Therefore, it may be advantageous to patient and clinician to implant electrodes at a site that is near the nerve or other target tissue using a minimally invasive procedure that places the electrodes in a region that the target nerve is known to reside and subsequently map the location of the electrodes relative to the target nerve for the purposes of defining efficacious therapy using stimulation thresholds. For example, a clinician may know that a nerve runs longitudinally across a region of the patient's body, e.g., longitudinally up and down along the patient's neck and back of the skull. In such an example, the clinician may implant a lead including a number of electrodes through a percutaneous incision such that the lead is generally arranged transverse to the target nerve. The clinician may not know the position of particular electrodes on the lead relative to the nerve, but may have a high confidence that the lead crosses the nerve and thus that some electrodes will be placed in close proximity to the nerve. The clinician may then employ stimulation thresholds to map the location of particular electrodes on the lead relative to the nerve as part of a programming session after implantation.

In some examples, it may not be known at the time of implant which of several nerve targets will yield results. For example, in some patients stimulation of the greater occipital nerve may be more efficacious than stimulating the lesser occipital nerve, or vice versa. Mapping based on thresholds may provide information regarding the relative location of the electrodes and a number of nerves. Because of the possibility of stimulating multiple nerves with the electrodes, although mapping may provide suggestions of likely effective electrodes or electrode combinations, in some examples it may still be important to test the chosen electrodes and optimize stimulation parameters.

Such implantation and nerve mapping procedures may relate to and be particularly useful in the context of a number of different kinds of electrical stimulation therapy, including different kinds of neurostimulation therapies. For example, examples according to this disclosure may be applied in the context of cranial nerve stimulation (CNS) and peripheral nerve stimulation (PNS). In one example, the programming and stimulation techniques described in this disclosure may be employed to improve delivery of occipital nerve stimulation (ONS) to treat a variety of conditions, including, e.g., occipital neuralgia and chronic migraines.

In the foregoing manner, stimulation thresholds may be employed in the context of programming an IMD to deliver efficacious therapy to a patient by facilitating selection of stimulation parameters, e.g., stimulation amplitude and/or pulse width, and individual electrodes or combinations of electrodes that are likely to produce effective results for the patient. Additionally, stimulation thresholds may be employed to physically map the position of different electrodes within the body of the patient relative to the target tissue site, e.g., relative to a target nerve, thereby potentially reducing the costs, complexity, and risks of procedures used to implant the electrodes.

Examples according to this disclosure employ techniques for efficiently determining one or more thresholds for each of a number of implanted electrodes as a baseline for programming and delivering efficacious stimulation therapy to a patient via the electrodes. The disclosed examples also leverage the stimulation thresholds in the course of applying several techniques that may improve the method by which therapy is programmed, as well as the effectiveness of the therapy ultimately delivered based on such programming. For example, stimulation thresholds may be employed to cluster multiple individual electrodes or electrode combinations into a single stimulation program defining delivery of stimulation therapy to increase utilization of resources that may provide efficacious results to a patient.

In various examples consistent with the present disclosure, programming of an implantable stimulator includes determining at least one stimulation threshold for each of a number of implanted electrodes. In general, determining a threshold for an electrode may include gradually increasing the stimulation intensity provided by the electrode until the patient indicates feeling a particular sensation associated with the threshold being determined. Programming stimulation therapy can be time consuming due to, in some cases, the number of different variables that may be varied from one stimulation program to the next. For example, for stimulation delivered via a pair of stimulation leads, each of which includes eight electrodes, sometimes referred to as a 2×8 configuration, the number of possible electrode combinations is quite large, and may be over in the several thousands of unique combinations. In addition to testing different stimulation parameters and electrode combinations, in some cases, determining one or more stimulation thresholds for a number of implantable electrodes may also be time consuming. Because of the time required to program an IMD to deliver effective stimulation to a patient, even relatively small time savings achieved by efficient programming processes may have a significant impact. As such, examples according to this disclosure include programming techniques by which stimulation threshold(s) for a number of implanted electrodes may be determined quickly and efficiently.

In some examples, consistent with the present disclosure, the determination of stimulation thresholds for a number of electrodes is made more efficient by iteratively raising a baseline stimulation intensity from which to begin testing for thresholds, thereby decreasing the amount of time to ramp the stimulation from the baseline to the next stimulation threshold. In one example, the determination of a first stimulation threshold for one of a number of electrodes includes increasing the stimulation intensity provided to each of the plurality of electrodes from zero until the patient indicates that the first stimulation threshold has been reached. The physician, clinician, or other individual running a programming protocol, then determines which of the electrodes delivered the stimulation that resulted in the perception by the patient of the threshold, e.g., by activating each of the electrodes individually at the stimulation intensity at which the patient indicated the threshold had been reached until the electrode that produces the first threshold is identified. In some examples, after the first stimulation threshold is reached, the electrode associated with the first stimulation threshold is turned OFF for the remainder of the process of determining the same type of stimulation threshold. For example, while determining perception thresholds, the electrode associated with the first perception threshold is turned OFF until each of the remaining electrodes has been associated with a perception threshold. After the first threshold and the electrode producing the first electrode have been determined, stimulation may be increased for the remaining electrodes until the patient indicates that a second stimulation threshold has been reached. For the second threshold, however, stimulation may be increased from the stimulation intensity associated with the first threshold, instead of from zero. After the second threshold is determined, the electrode that produced the second threshold is determined, e.g., in a similar manner as described above with reference to the first stimulation threshold, and the electrode may similarly be turned OFF. This process may be repeated iteratively until one or more stimulation thresholds are determined for each of the electrodes.

In some examples, all thresholds of a particular type are determined for each of the electrodes before moving on to another type of threshold. For example, a perception threshold may be determined for each of the electrodes before testing for a higher stimulation intensity threshold like pain or discomfort thresholds. In another example, however, the iterative process set forth above may include determining a number of different types of thresholds for different electrodes being tested. For example, a perception threshold may be determined for a number of electrodes being tested, while parasthesia and/or another type of threshold is determined for a number of other electrodes being tested.

In some examples, instead of determining all thresholds of a particular type for each of the electrodes before moving on to another type of threshold, a number of stimulation thresholds are determined for each electrode before moving on to the next electrode. For example, the first stimulation threshold determined for one electrode may be a perception threshold, and the remaining stimulation thresholds for the electrode that produces the first threshold may be determined iteratively, e.g., by increasing the stimulation intensity provided by the electrode from the intensity that produced the first perception threshold until a second threshold is reached, and then increasing the stimulation intensity from the intensity that produced the second threshold until a third threshold is reached, and so on before determining any stimulation thresholds for any other electrode. In some examples the second threshold for an electrode may be the parasthesia threshold. After identification of the parasthesia threshold, the stimulation intensity may be increased from the parasthesia threshold to a third threshold, which may be a high or upper bound threshold beyond which stimulation is not increased. In some examples, an electrode may not have a parasthesia electrode, and the second threshold may be an upper bound threshold. The high or upper bound threshold for an electrode may refer to a threshold associated with a sensation that is unpleasant to such a degree that it is undesirable to provide stimulation therapy to a patient at or above that level of intensity. In contrast to the upper threshold, a lower threshold for an electrode may refer to a threshold associated with a stimulation intensity at which a patient first perceives an effect of the stimulation, e.g., first feels the stimulation or first perceives a parasthesia or "tingling" feeling. In some cases, the lower and upper threshold may be one threshold, e.g., where the first effect of stimulation felt by the patient is pain or discomfort. As noted above, example lower stimulation thresholds include the perception and parasthesia thresholds and example high stimulation thresholds include the discomfort, muscle recruitment, and pain thresholds.

In examples in which the upper threshold is a muscle recruitment threshold, the stimulation may be increased beyond this threshold during programming until a pain or discomfort threshold is reached. The range between the muscle recruitment threshold and the pain or discomfort threshold may be used for stimulation testing and therapy in certain limited circumstances. For example, during a short period of time before a migraine where the discomfort of the muscle recruitment may be outweighed by the added therapeutic benefits of a higher stimulation intensity. In some examples, after the various stimulation thresholds are determined for the first electrode, the stimulation provided by a second electrode is increased from the perception threshold, or other lower threshold of the first electrode, until each of the thresholds associated with the second electrode are determined. This may be repeated until the thresholds for each of the plurality of electrodes is determined. In one example, testing for each successive electrode may begin by increasing stimulation intensity from the first identified lower stimulation threshold. In another example, testing for each successive electrode may begin by increasing stimulation intensity from the lower stimulation threshold for the previously tested electrode.

In some examples, a lower threshold determination for each of the electrodes is used to determine which of the electrodes to test for additional thresholds. For example, if the perception threshold is above a predetermined level, it may be unnecessary to test for an upper threshold because of the low likelihood of using the electrode. The relatively high level of the lower threshold may indicate that the electrode is too far from the nerve to be of use. In other examples, the lower threshold may be too close to the maximum stimulation intensity that may be provided by the IMD to provide an adequate usability range.

In other examples, one or more electrodes may not have any stimulation thresholds. For example, an electrode may be located too far from the target nerve to be perceived even at the highest stimulation intensity. In such examples, it may be desirable to disqualify the electrode as a possible electrode for providing stimulation therapy.

Examples consistent with the present disclosure include storing the identified stimulation thresholds, including the perception threshold, the paresthesia threshold and an upper threshold. The stored thresholds may be used by a processor to create programs to provide stimulation therapy. The thresholds may also be used to limit changes a patient may make to the stimulation therapy using a patient programmer. In various examples consistent with the present disclosure the various stimulation thresholds may be used to perform a variety of tasks.

As noted above, examples according to this disclosure may employ stimulation thresholds to cluster multiple individual electrodes or electrode combinations into a single stimulation program defining delivery of stimulation therapy to increase utilization of resources that may provide efficacious results to a patient. Clustering may occur after the determination of the stimulation thresholds, after the determination of the usability range, after the mapping of the relative locations of the electrodes and the nerve. In general, clustering involves determining if one or more electrodes have similar characteristics that allow for stimulation to be provided to the nerve using the electrodes and the same stimulation program. In some examples, electrodes may be clustered based on one or more stimulation threshold. For example, electrodes with similar paresthesia thresholds may be clustered together. In some examples, after a clustering based on paresthesia thresholds, electrodes with a usability range under a certain value may be removed from the cluster. This allows for the program to use multiple electrodes at once with ranges over a particular level while still allowing a single source to drive the multiple electrodes.

In some examples, an electrode is chosen to provide stimulation therapy. The programmer may then attempt to create a cluster of electrodes including the chosen electrode based on the paresthesia threshold of the chosen electrode. The programmer first determines which electrodes have a paresthesia threshold approximately equal to the paresthesia threshold of the chosen electrode. In some examples, the paresthesia thresholds of the other electrodes are within a predetermined range of the paresthesia threshold associated with the chosen electrode. The programmer may then select those electrodes with similar paresthesia thresholds that have a usability range at least as large as that of the chosen electrode. This allows the chosen electrode to be used across its entire usability range while still allowing for clustering of electrodes when the implantable stimulator has a single source, or a number of sources that is less than the number of electrodes within the cluster, or the user wishes to minimize the complexity of use for the patient by minimizing the number of programs that must be independently controlled.

In another example, as noted above, stimulation thresholds are employed to map the location of electrodes relative to a target nerve, which mapping may be used for visualization and automated selection of efficacious electrode combinations. These and other techniques described below are also employed in combination to program and maintain, over time, the delivery of efficacious stimulation therapy to a patient to treat one or more conditions.

In some examples, the implantable stimulator may be connected to an array of electrodes. In some examples, the array of electrodes may be on a paddle lead. In other examples, the array of electrodes may be on a plurality of leads, where the relative location of each of the leads is known. In examples where there implantable stimulator is connected to an array of leads, the relative location of the nerve and the electrodes may be determined in more detail. For example, information about the relative locations may be derived in both an X and a Y direction. In another example, information about the relative locations may be derived in X, Y, and Z directions such that the orientation in space is substantially completely known.

In some examples, more than one cluster of electrodes or electrodes may be selected to provide stimulation. For example, an implantable stimulator may be able to provide stimulation therapy based on a plurality of stimulation programs. Each of the stimulation programs may be associated with the same, or different, electrodes. In some examples, the implantable stimulator may include up to 4 programs.

In some examples, the effectiveness of stimulation therapy may change over time. In some examples, the change may be in response to recurring changes in the electrodes position. For example, when a patient turns his or her head, the relative location of the electrodes and the nerve may change. In some examples, different stimulation thresholds may be detected for different head positions, and the implantable stimulator may store modifications to one or more stimulation therapy programs to be implemented in response to detection of a change in head position. In one example, a patient may have a patient programmer, which may be employed to modify and program the stimulation parameters for different positions of the patient's head. Programming adaptive stimulation based on head position may also be accomplished under the supervision of a clinician. At any rate, the implantable stimulator may then store the new program settings and reuse the setting each time the same position is detected.

In some examples, a permanent change may occur in the relative location of the electrodes and the nerve within a patient. For example, over time, the electrodes and the lead to which they are attached may migrate within the body of the patient, thus changing the location of the nerve relative to particular electrodes. In some examples, a subset of the electrodes may be retested for stimulation thresholds when a change in relative position is suspected. The new stimulation thresholds for the subset of electrodes tested may be compared to the old stimulation thresholds. Based on the comparison an automatic change to the stimulation program may be made. In some examples, the comparison may indicate that all of the thresholds need to be re-determined before a new program is created.

The various electrical stimulation programming and therapy delivery techniques included in examples according to this disclosure are described in detail with reference to FIGS. 8-17. However, example electrical stimulation systems including, e.g., implantable stimulators, stimulation leads and electrodes, and external programmers through which such techniques may be applied are first described with reference to FIGS. 1A-7.

FIG. 1A is a conceptual diagram illustrating an example therapy system 10A that includes an implantable medical device (IMD) 12 configured as an electrical stimulator, which is coupled to implantable stimulation leads 14 and 15. In the example of FIG. 1A, IMD 12 is implanted proximate to target stimulation sites 18 and 19 within patient 16. In one example, target stimulation sites 18 and 19 are proximate to an occipital region 11 within patient 16. Occipital region 11 generally encompasses occipital nerve sites and trigeminal nerve sites of patient 16, which may be, for example, an occipital nerve (e.g., a greater occipital nerve, lesser occipital nerve, or third occipital nerve), a trigeminal nerve, tissue adjacent to the trigeminal or occipital nerves, or a nerve branching from the occipital and/or trigeminal nerves. Thus, reference to an "occipital nerve" or a "trigeminal nerve" throughout the disclosure also includes branches of the occipital and trigeminal nerves, respectively. Similarly reference to a "trigeminal nerve" throughout the disclosure also includes branches of one of the three major divisions of the trigeminal nerve. In addition, the therapy may be delivered to both an occipital nerve and trigeminal nerve by a single therapy system or by separate therapy systems (e.g., by separate electrical stimulators and leads).

IMD 12 provides a programmable stimulation signal (e.g., in the form of electrical pulses or substantially continuous-time signals) that is delivered to target stimulation sites 18 and 19 by implantable medical leads 14 and 15, respectively, and more particularly, via stimulation electrodes carried by leads 14 and 15. IMD 12 may also be referred to as a pulse or signal generator, and in the example shown in FIG. 1, IMD 12 may also be referred to as a neurostimulator. In some examples, lead 14 and/or lead 15 may also carry one or more sense electrodes to permit IMD 12 to sense electrical signals or other physiological parameters (e.g., blood pressure, temperature, etc.) from target stimulation site 18 and/or 19, respectively. Additionally, IMD 12 may operate in conjunction with other sensors housed by IMD 12 or separate from the device and configured to sense patient parameters, including, e.g., patient posture, activity level, and/or head position. Such conditions may affect the efficacy of stimulation therapy and sensing these conditions may therefore provide feedback signals for closed loop stimulation therapy that automatically changes as a function of one or more of the sensed conditions. For example, IMD 12 may work in conjunction with one or more accelerometers implanted within patient 16 to provide posture responsive stimulation therapy that automatically adjusts based on the posture of the patient sensed by the accelerometers. In another example, IMD 12 may work in conjunction with one or more accelerometers or other sensors configured to sense the position or orientation of the head of patient 16 relative to the patient's torso to provide stimulation therapy that automatically adjusts based on head position. Example techniques for providing adaptive stimulation therapy to a patient based on head position are described in commonly-assigned U.S. Provisional Application No. 61/481,032, filed Apr. 29, 2011, and U.S. patent application No. 13/457,063, filed Apr. 26, 2012, entitled "ELECTRICAL STIMULATION THERAPY BASED ON HEAD POSITION," and issued as U.S. Pat. No. 9,649,494 on May 16, 2017, which claims the benefit of U.S. Provisional Application No. 61/481,032, the entire contents of both of which are incorporated herein by reference.

Proximal ends 14A and 15A of leads 14 and 15, respectively, may be both electrically and mechanically coupled to connection ports of connector block 13 of IMD 12 either directly or indirectly (e.g., via a lead extension). In particular, conductors disposed in the lead body of each of leads 14 and 15 may electrically connect stimulation electrodes (and sense electrodes, if present) adjacent to distal ends 14B and 15B of leads 14 and 15, respectively, to IMD 12.

In the example of therapy system 10A shown in FIG. 1A, target stimulation sites 18 and 19 are located within the patient's head (e.g., proximate to one or more occipital nerve) and on opposite sides of midline 9 of patient 16. Midline 9 is a schematic representation of the line that divides patient 16 into approximately equal and symmetrical left and right halves. Delivering therapy to two target tissue sites, such as sites 18 and 19, may be used to deliver therapy to two nerve branches that branch from the same nerve. Patient 16 may have mirror nerves that extend on opposite sides of midline 9, and therapy may be delivered to one or both of the nerves on opposite sides of midline 9 (such as at target tissue sites 18 and 19). A Nerve may also one or more nerve branches. Stimulation of two nerves on opposite sides of midline 9 may be referred to as bilateral stimulation. However, bilateral stimulation may also refer to stimulation of any two regions of patient 16 either sequentially or simultaneously. Delivering therapy at or near nerve branches, e.g., closer to the nerve endings, may allow more targeted therapy delivery with fewer side effects.

Stimulation of the occipital region 11 (i.e., in regions of patient 16 proximate to occipital nerves, a trigeminal nerve or other cranial sites) may help alleviate pain associated with, for example, chronic migraines, cervicogenic headaches, occipital neuralgia or trigeminal neuralgia.

Therapy system 10A, however, is useful in other neurostimulation applications. Thus, in other examples, target stimulation sites 18 and 19 may be at locations proximate to any other suitable nerve in body of patient 16, which may be selected based on, for example, a therapy program selected for a particular patient. In other examples, therapy system 10 may be used to deliver neurostimulation therapy to other areas of the nervous system, in which cases, lead 14 would be implanted proximate to the respective nerve(s). As one example, leads 14 and 15 may be implanted proximate to other nerves and/or structures of the head and neck of patient 16. For example, when therapy system 10 is used for stimulating a trigeminal nerve, target stimulation sites 18 and 19 may be on the side or front of the head of patient 16. In another example, IMD 12 and one or both of leads 14 and 15 may be directed to CNS targeting cranial nerves other than the occipital or trigeminal nerves, including, e.g., a supraorbital nerve. In another example, threshold determinations, stimulation programming and therapy delivery techniques according to this disclosure may be directed to stimulation of one or more peripheral nerves, including, e.g., sacral nerves for the treatment of various conditions including urinary tract dysfunction such as urinary incontinence.

In the illustrated example of FIG. 1A, IMD 12 is implanted in the back of patient 16 over the trapezius muscle (e.g., IMD 12 may be disposed within a surgically formed subcutaneous pocket formed near the trapezius muscle). IMD 12 may be inserted into patient 16 at incision site 17A.

Leads 14 and 15 may also be inserted into patient 16 at incision site 17A and advanced (e.g., by tunneling) to target tissue sites 18 and 19, respectively. In this manner, IMD 12, lead 14, and lead 15 may all be inserted using a single incision at incision site 17A. Alternatively, a second incision may be made at incision site 17B to facilitate implantation of leads 14 and 15 within patient 16 and positioning leads 14 and 15 with respect to target tissue sites 18 and 19 to achieve useful stimulation therapy or sensing. In another example, IMD 12 may be implanted at other suitable locations within patient 16, such as but not limited to, in a chest cavity, lower back, lower abdomen, or buttocks of patient 16.

Therapy system 10A also may include a clinician programmer 26 and a patient programmer 28. In another example, system 10A may include one external programmer that functions as both a physician and patient programmer, e.g., based on user credentials input by the user to access functions on the programmer. Clinician programmer 26 may be a handheld computing device that permits a clinician to program neurostimulation therapy for patient 16, e.g., using input keys and a display. For example, using clinician programmer 26, the clinician may initiate a protocol to determine stimulation thresholds for each electrode on leads 14 and 15. Based on the determined stimulation thresholds, the clinician may map the location of electrodes on leads 14 and 15 and specify stimulation parameters for use in delivery of electrical stimulation therapy. Clinician programmer 26 supports telemetry (e.g., radio frequency telemetry) with IMD 12 to download neurostimulation parameters and, optionally, upload operational or physiological data stored by IMD 12. In this manner, the clinician may periodically interrogate IMD 12 to evaluate efficacy and, if necessary, modify the stimulation parameters.

Like clinician programmer 26, patient programmer 28 may be a handheld computing device. Patient programmer 28 may also include a display and input keys to allow patient 16 to interact with patient programmer 28 and IMD 12. In this manner, patient programmer 28 provides patient 16 with an interface for control of neurostimulation therapy by IMD 12. For example, patient 16 may use patient programmer 28 to start, stop or adjust neurostimulation therapy. In particular, patient programmer 28 may permit patient 16 to adjust stimulation parameters such as duration, amplitude, pulse width and pulse rate, within an adjustment range specified by the clinician via clinician programmer 28, or select from a library of stored stimulation therapy programs.

IMD 12, clinician programmer 26, and patient programmer 28 may communicate via cables or a wireless communication, as shown in FIG. 1A. Clinician programmer 26 and patient programmer 28 may, for example, communicate via wireless communication with IMD 12 using known RF telemetry techniques, including, e.g., RF communication according to the 802.11 or Bluetooth specification sets, or other wireless communication techniques, including infrared communication, e.g., according to the IrDA standard, or other standard or proprietary telemetry protocols.

However, clinician programmer 26 and patient programmer 28 need not communicate wirelessly. For example, in other examples, programmers 26 and 28 may communicate via a wired connection, such as via a serial communication cable, or via exchange of removable media, such as magnetic or optical disks, or memory cards or sticks. Further, the clinician programmer 26 may communicate with patient programmer 28 via remote telemetry techniques, or via a local area network (LAN), wide area network (WAN), public switched telephone network (PSTN), or cellular telephone network, for example.

Stimulation thresholds for one or more electrodes on one or both of leads 14 and 15 may be employed in the context of programming IMD 12, e.g., via clinician programmer 26 and/or patient programmer 28 to deliver efficacious therapy to patient 16 by facilitating selection of stimulation parameters, e.g., stimulation amplitude and/or pulse width, and individual electrodes or combinations of electrodes that are likely to produce effective results for the patient. Additionally, stimulation thresholds may be employed to physically map the position of different electrodes on leads 14 and 15 within the body of patient 16 relative to target stimulation sites 18 and 19, e.g., relative to one or more occipital nerves, thereby potentially reducing the costs, complexity, and risks of procedures used to implant IMD 12 and leads 14 an 15.

In one example, clinician programmer 26, or another external programmer communicatively connected to IMD 12, e.g., patient programmer 28 is employed to determine a stimulation threshold for each electrode connected to leads 14 and 15 arranged adjacent target stimulation sites 18 and 19, e.g., adjacent one or more occipital nerves of patient 16. Programmer 26 and/or IMD 12 may be configured to map the location of the target occipital nerve(s) relative to the electrodes of leads 14 and 15 based on the stimulation threshold of each of the electrodes. A clinician may employ programmer 26 to select an individual electrode or combination of electrodes on one or both of leads 14 and 15 through which IMD 12 may provide stimulation to the occipital nerve(s) at or near target stimulation sites 18 and 19 based, at least in part, on the location of the nerve relative to the selected electrode or electrode combination. In one example, the clinician also employs programmer 26 to create a stimulation program according to which IMD 12 may provide stimulation to the occipital nerve via the selected electrode or electrode combination. The stimulation program may include various values for different stimulation parameters, including, e.g., stimulation amplitude, pulse width, and frequency. In one example, the program is created and stored on programmer 26, in which case programmer 26 may transmit the stimulation program to patient programmer 28 and/or IMD 12. IMD 12 may deliver stimulation to occipital nerve(s) of patient 16 via electrodes on lead 14 and/or 15 according to the stimulation program in order to test the efficacy of the program or to provide chronic therapy to the patient to treat symptoms of one or more conditions, e.g., occipital neuralgia or chronic migraines.

Examples according to this disclosure employ programming techniques for efficiently determining one or more thresholds for each of a number of electrodes associated with leads 14 and 15 as a baseline for programming IMD 12 and controlling IMD 12 to deliver efficacious stimulation therapy to patient 16 via the electrodes. In one example, IMD 12 increases a stimulation intensity for each of a plurality of electrodes from a baseline intensity level until a first stimulation threshold is reached. A patient or clinician, using clinician programmer 26 or patient programmer 28, identifies a first electrode that produced the first stimulation threshold. The programmer then associates the first stimulation threshold with the first electrode. IMD 12 increases the stimulation intensity from the first stimulation threshold until a second stimulation threshold is reached. In some examples, the programmer 26 is again used to identify an electrode responsible for the second stimulation threshold. The steps of increasing stimulation intensity until a threshold is reached, identifying an electrode responsible for the threshold, and association of the electrode with the threshold may be repeated until each electrode has been associated with a threshold. Various methods of determining stimulation thresholds consistent with the present disclosure are discussed in more detail below with respect to FIG. 9, for example.

The disclosed examples also leverage the stimulation thresholds determined according to the foregoing techniques in an effort to improve the method by which therapy delivered by IMD 12 is programmed, e.g., by clinician programmer 26, as well as the effectiveness of the therapy ultimately delivered to patient 16 based on such programming. For example, stimulation thresholds for one or more electrodes associated with leads 14 and 15 connected to IMD 12 may be employed to cluster multiple individual electrodes or electrode combinations into a single stimulation program defining delivery of stimulation therapy to increase utilization of resources that may provide efficacious results to patient 16. In one example, programmer 26 clusters a plurality of electrodes based on at least one of threshold or usability range, wherein the usability range of stimulation delivered by one or more electrodes is defined by a difference between a paresthesia threshold and a discomfort threshold for the one or more electrodes. IMD 12 delivers stimulation to a nerve of a patient via the cluster of electrodes. Various methods of clustering electrodes consistent with the present disclosure are discussed in more detail below with respect to FIGS. 15 and 16.

As described generally above, stimulation thresholds may be employed to map the location of electrodes connected to leads 14 and/or 15 relative to a target nerve, e.g., relative to one or more occipital nerves of patient 16. Nerve mapping may subsequently be used to for visualization, e.g., to display a representation of the target nerve or nerves and one or both of leads 14 and 15 on a display of clinician programmer 26 and/or patient programmer 28. Nerve mapping based on stimulation thresholds for electrodes connected to leads 14 and/or 15 may also be employed to automatically select individual electrodes or electrode combinations for stimulation testing and/or chronic therapeutic stimulation delivery. In one example, IMD 12 applies stimulation to a nerve via each of a plurality of implantable electrodes arranged proximate to a target nerve. IMD 12 or programmer 26 determines an effect of the stimulation for each of the electrodes. Programmer 26 maps a location of the nerve relative to the electrodes based on the effect of the stimulation for each of the electrodes. In some examples, the programmer 26 determines at least one threshold for each electrode based on patient feedback. Various examples of nerve mapping consistent with the present disclosure are discussed in more detail below with respect to FIGS. 10-12.

In some examples according to this disclosure, one or more combinations of the foregoing techniques are combined into a process by which IMD 12 may be programmed to deliver efficacious therapy to patient 16, e.g., employing one or both of clinician programmer 26 and patient programmer 28. In one example, one or both of clinician programmer 26 and patient programmer 28 may be employed to determine a stimulation threshold for each of a number of electrodes connected to one or both of leads 14 and 15. For example, clinician programmer 26 may be employed in the manner summarized above to determine a number of stimulation thresholds by iteratively increasing stimulation from a baseline stimulation intensity until patient 16 indicates a stimulation threshold has been reached. Programmer 26 and/or IMD 12 may also map the location of a target nerve or other tissue relative to the electrodes connected to one or both of leads 14 and 15 based on the stimulation threshold of each of the electrodes. Programmer 26 and/or IMD 12 may select at least one of the electrodes through which to provide stimulation to the nerve based at least in part on the location of the nerve relative to the electrode and create a program according to which stimulation may be delivered to patient 16 via the selected electrode(s). The stimulation program may be stored on one or more of clinician programmer 26, patient programmer 28, and IMD 12 and may be executed to control IMD 12 to deliver the stimulation by one or more of these devices.

Figure 1B:
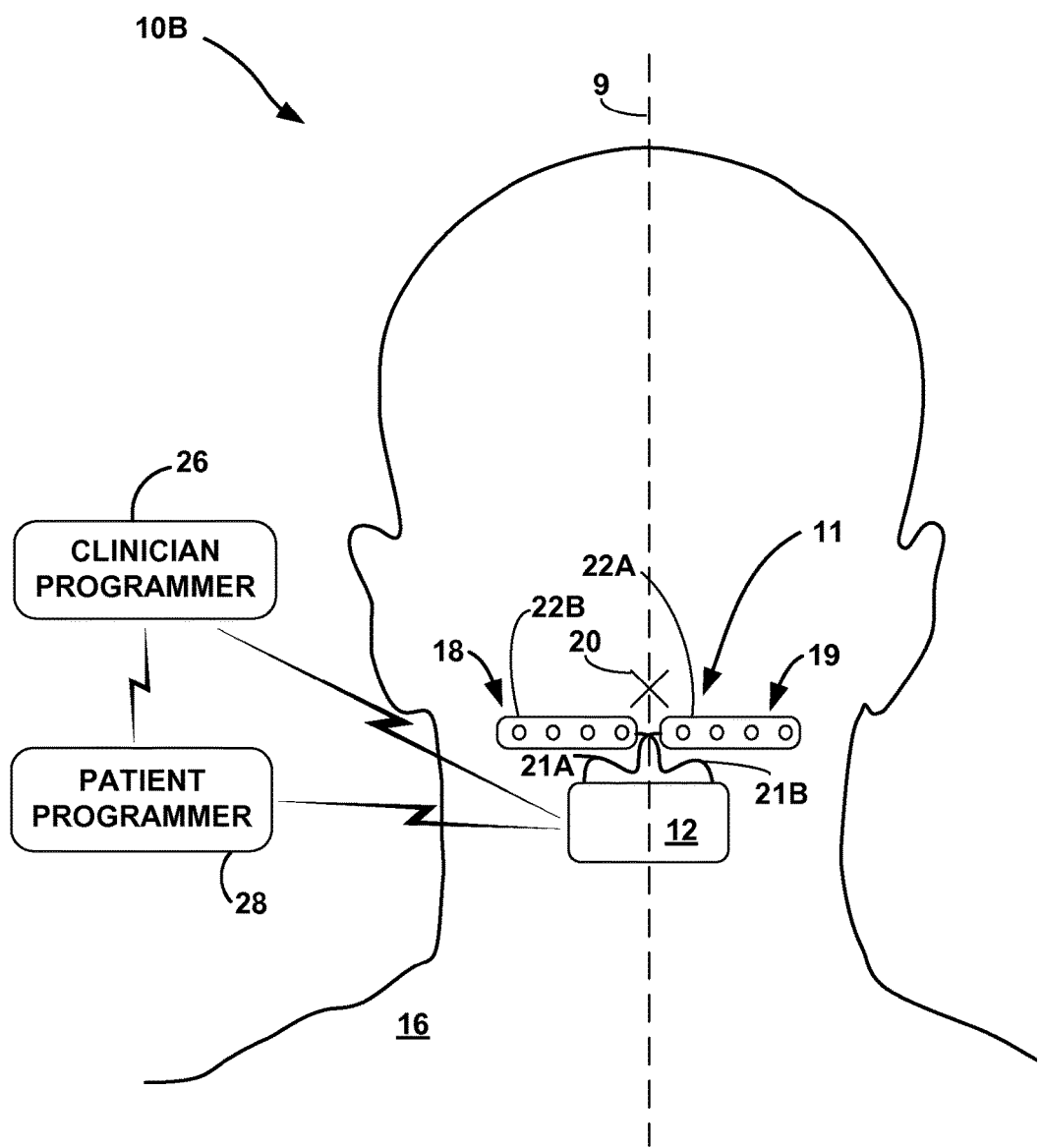

FIG. 1B is a conceptual diagram illustrating an example therapy system 10B that includes an implantable IMD 12 coupled to implantable stimulation leads 21A and 21B connected to paddles 22A and 22B (collectively referred to as "paddles 22"), respectively. In the example of FIG. 1B, IMD 12 is implanted in a human patient 16 proximate to an occipital region 11 within patient 16, below inion 20, the craniometric point that is the most prominent point at the occipital protuberance on the back of the head of patient 16. Similar to leads 14 and 15 of FIG. 1A, paddles 22 include electrode sets to deliver stimulation therapy to a therapy region, which generally encompasses occipital nerve sites and trigeminal nerve sites of patient 16. Various techniques as discussed above with respect to FIG. 1A may be employed using therapy system 10B. In some instances, minor modifications may be made, for example, in instances where paddles 22 may include more than one row of electrodes. Examples using multiple rows of electrode are discussed in more detail below with respect to FIG. 12, for example.

Figure 2:
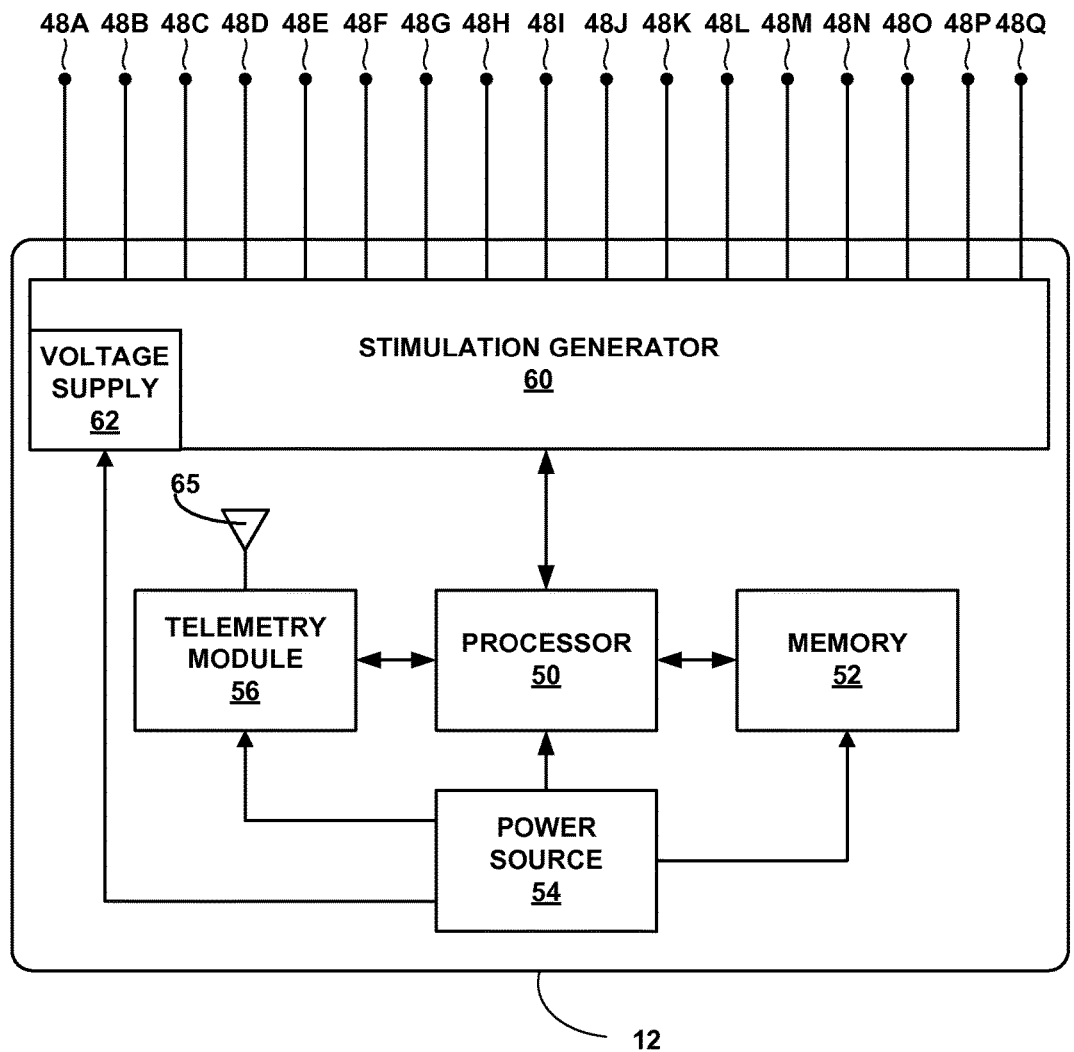
FIG. 2 is a block diagram illustrating various example components of an implantable electrical stimulator.

FIG. 2 is a block diagram illustrating various components of an example configuration of IMD 12 in system 10. In some cases, the components of FIG. 2 may be implemented in an external stimulator. In the example of FIG. 2, IMD 12 includes processor 50, memory 52, power source 54, telemetry module 56, antenna 65, and a stimulation generator 60. IMD 12 is also shown in FIG. 2 coupled to electrodes 48A-Q (collectively "electrodes 48").

Processor 50 may include one or more microprocessors, digital signal processors (DSPs), application-specific integrated circuits (ASICs), field-programmable gate arrays (FPGAs), or other digital logic circuitry. Processor 50 controls operation of IMD 12, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with pulse current amplitudes (i.e., levels), pulse widths (if applicable), and pulse rates specified by one or more stimulation programs.

Memory 52 may store instructions for execution by processor 50, stimulation therapy data, sensor data, and/or other information regarding therapy for patient 16. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and in this disclosure. For example, memory 52 may store one or more stimulation programs based, at least in part, on one or more stimulation thresholds and executable by processor 50 to control stimulation generator 60 to deliver stimulation to patient 16 via one or more of electrodes 48. In one example, memory 52 may also store stimulation thresholds for one or more of electrodes 48, electrode clustering information, as well as information related to the location of one or more of electrodes 48 relative to a target nerve or group of nerves or other tissue.

Stimulation generator 60 forms a therapy delivery module of IMD 12. Processor 50 controls stimulation generator 60 to deliver electrical stimulation via electrode combinations formed by electrodes 48A-Q. For example, stimulation generator 60 may deliver electrical stimulation therapy via electrodes on one or more of leads 14 and 15, e.g., as stimulation pulses or continuous waveforms. Stimulation generator 60 may include stimulation generation circuitry to generate stimulation pulses or waveforms and switching circuitry to switch the stimulation across different electrode combinations, e.g., in response to control by processor 50. In particular, processor 50 may control the switching circuitry on a selective basis to cause stimulation generator 60 to deliver electrical stimulation to selected electrode combinations and to shift the electrical stimulation to different electrode combinations when the therapy is delivered to a different locations within patient 16. In other examples, stimulation generator 60 may include multiple current sources to drive more than one electrode combination at one time. In this case, stimulation generator 60 may decrease current to the first electrode combination and simultaneously increase current to the second electrode combination to shift the stimulation therapy.

An electrode configuration, e.g., electrode combination and associated electrode polarities, may be represented by data stored in a memory location, e.g., in memory 52, of IMD 12. Processor 50 may access the memory location to determine the electrode combination and control stimulation generator 60 to deliver electrical stimulation via the indicated electrode combination. To adjust electrode combinations, amplitudes, pulse rates, or pulse widths, processor 50 may command stimulation generator 60 to make the appropriate changes to therapy according to instructions within memory 52 and rewrite the memory location to indicate the changed therapy. In other examples, rather than rewriting a single memory location, processor 50 may make use of two or more memory locations.

When activating stimulation, processor 50 not only accesses the memory location specifying the electrode combination but also other memory locations specifying various stimulation parameters such as voltage or current amplitude, pulse width and pulse rate. Stimulation generator 60, e.g., under control of processor 50, then makes use of the electrode combination and parameters in formulating and delivering the electrical stimulation to patient 12.

Stimulation generator 60 forms a therapy delivery module of IMD 12. Processor 50 controls stimulation generator 60 to deliver electrical stimulation via electrode combinations formed by electrodes 48. For example, stimulation generator 60 may deliver electrical stimulation therapy via electrodes on one or more of leads 14 and 15, e.g., as stimulation pulses or continuous waveforms. Stimulation generator 60 may include stimulation generation circuitry to generate stimulation pulses or waveforms and switching circuitry to switch the stimulation across different electrode combinations, e.g., in response to control by processor 50. In particular, processor 50 may control the switching circuitry on a selective basis to cause stimulation generator 60 to deliver electrical stimulation to selected electrode combinations and to shift the electrical stimulation to different electrode combinations when the therapy is delivered to a different locations within patient 16. In other examples, stimulation generator 60 may include multiple current sources to drive more than one electrode combination at one time. In this case, stimulation generator 60 may decrease current to the first electrode combination and simultaneously increase current to the second electrode combination to shift the stimulation therapy.

An electrode configuration, e.g., electrode combination and associated electrode polarities, may be represented by data stored in a memory location, e.g., in memory 52, of IMD 12. Processor 50 may access the memory location to determine the electrode combination and control stimulation generator 60 to deliver electrical stimulation via the indicated electrode combination. To adjust electrode combinations, amplitudes, pulse rates, or pulse widths, processor 50 may command stimulation generator 60 to make the appropriate changes to therapy according to instructions within memory 52 and rewrite the memory location to indicate the changed therapy. In other examples, rather than rewriting a single memory location, processor 50 may make use of two or more memory locations.

When activating stimulation, processor 50 not only accesses the memory location specifying the electrode combination but may also access other memory locations specifying various stimulation parameters such as voltage or current amplitude, pulse width and pulse rate. Stimulation generator 60, e.g., under control of processor 50, then makes use of the electrode combination and parameters in formulating and delivering the electrical stimulation to patient 12. Particular electrode combinations and stimulation parameters, e.g., amplitude, pulse width, and frequency may be collected in a stimulation program, as described in more detail below, which may be stored in memory 52 and executed by processor 50 to control stimulation generator 60 to deliver therapy to patient 16.

Stimulation generator 60 may delivery therapy via electrodes 48A-48Q in response to a signal received by telemetry module 56 from an external programmer 26 or 28. In some examples a signal received from patient programmer 28, for example, may cause processor 50 to modify one or more stimulation parameters used to deliver stimulation therapy. In some examples, patient 16 may increase or decrease the stimulation intensity. In some examples, telemetry module 56 may receive a signal from one or more accelerometers implanted in patient 16, based on the information from the accelerometers processor 50 may retrieve different stimulation parameters to be applied by stimulation generator 60. In other examples, one or more accelerometers may be attached directly to IMD 12 and processor 50 may receive signals from the accelerometers directly and, based thereon, retrieve different stimulation parameters to be applied by stimulation generator 60.

An exemplary range of electrical stimulation parameters likely to be effective in treating the effects of symptoms of a chronic condition related to one or more nerves of patient 16, e.g., pain associated with migraine headaches or occipital or trigeminal neuralgia, are listed below. While stimulation pulses are described, stimulation signals may be of any of a variety of forms such as sine waves, stepped square waves, sawtooth or triangular waveforms, biphasic pulse pairs, or the like.

1. Pulse Rate: between approximately 4 Hz and approximately 1200 Hz, more preferably between approximately 4 Hz and approximately 130 Hz, and still more preferably between approximately 40 Hz and approximately 80 Hz.

2. Amplitude: between approximately 0.1 volts and approximately 10.5 volts. In other examples, the amplitude may be specified or measured in terms of a current amplitude that is delivered to the patient. For example, the range of current amplitude may be between approximately 0.1 milliamps (mA) and approximately 20 mA.

3. Pulse Width: between approximately 10 microseconds and approximately 1000 microseconds, more preferably between approximately 80 microseconds and approximately 400 microseconds.

Depending on the application, different ranges of parameter values may be used by IMD 12, and, in particular, processor 50 to control stimulation generator 60 to deliver stimulation via one or more of electrodes 48 on leads 14 and/15 to patient 16.

Processor 50 accesses stimulation parameter values stored by memory 52, e.g., as therapy programs and groups of programs. In some examples, the stored programs and program groups may be arranged differently. For example, a given program group may be made up of four different programs. However, the programs that make up the program group may be selected by a user via programmer 26 or 28. In some examples a patient may be able to change the programs within the program groups based on current symptoms. Upon selection of a particular program or program group, processor 50 controls stimulation generator 60 to deliver stimulation according to the programs in the groups, e.g., simultaneously or on a time-interleaved basis. A therapy group may include a single program or multiple programs. In one example, one program group may include multiple prophylactic stimulation programs and another program group stored on memory 52 and executable by processor 50 may include multiple abortive stimulation programs. As mentioned previously, each therapy program specifies values for a set of stimulation parameters, such as amplitude, pulse width, and pulse rate. In addition, each program may specify a particular electrode combination for delivery of stimulation. Again, the electrode combination may specify particular electrodes in a single array or multiple arrays, e.g., particular combinations of electrodes 48A-Q on leads 14 and/or 15.

In some examples, processor 50 may control stimulation generator 60 to deliver electrical signals to electrodes 48 during a programming protocol that may be configured to determine one or more efficacious stimulation therapy programs according to which stimulation generator 60 may deliver chronic therapy to patient 16. As described in this disclosure, an initial programming protocol may be implemented using either clinician programmer 26 or patient programmer 28. In one example, during the initial programming protocol at least one stimulation threshold is determined for each of electrodes 48. The stimulation thresholds may be determined based on patient feedback provided to processor 50 via external programmer 26 or programmer 28 and may be stored in memory 52.

Based on stimulation threshold(s) for one or more of electrodes 48, the relative location of the electrodes and at least one nerve may be determined or "mapped." In some examples, processor 50 maps the relative location of the electrodes and the target nerve, and stores the information in memory 52. In some examples, stimulation generator 60 provides stimulation to a subset of electrodes 48 that are chosen based on the mapping. In some examples, the choice of electrodes may be made by a clinician via programmer 26. In other examples, the electrodes may be chosen automatically by IMD 12, clinician programmer 26 or patient programmer 28. In some examples, other information, including for example, a usability range calculated by processor 50 in IMD 12, or by clinician programmer 26 or patient programmer 28, is used in selecting the electrodes.

In some examples, a number of electrodes 48 may be clustered together. For example, processor 50 may identify and group, or cluster, one or more individual electrodes 48 or electrode combinations selected from electrodes 48 with similar stimulation thresholds, e.g., similar lower stimulation thresholds like perception or paresthesia thresholds. Processor 50 may, in different circumstances, control stimulation generator 60 to deliver electrical stimulation to patient 16 via the clustered electrodes. In some examples, clusters of electrodes may be chosen based on usability range, i.e. multiple stimulation thresholds and the range of stimulation intensities there between, as well as based on the direction of stimulation produced by multiple electrodes or electrode combinations. In other examples, electrodes may be clustered based on similarity of outcome or the nature of the upper threshold. For example, electrodes that all cause muscle recruitment at some stimulation intensity level may be more suitable for clustering than clustering electrodes with a muscle recruitment upper threshold with electrodes with a pain upper threshold.

In some examples according to this disclosure, one or more combinations of the foregoing techniques are combined into a process by which IMD 12 may be programmed to deliver efficacious therapy to patient 16, e.g., employing one or both of clinician programmer 26 and patient programmer 28. In one example, one or both of clinician programmer 26 and patient programmer 28 may be employed to determine a stimulation threshold for each of a number of electrodes connected to one or both of leads 14 and 15. For example, clinician programmer 26 may be employed in the manner summarized above to determine a number of stimulation thresholds by controlling stimulation generator 60 of IMD 12 via a telemetry connection utilizing telemetry module 56 to iteratively increase stimulation from a baseline stimulation intensity until patient 16 indicates a stimulation threshold has been reached. Stimulation thresholds, after being determined, may be stored in memory 52 and/or memory included in one or both of clinician programmer 26 and patient programmer 28.

In one example, processor 50 of IMD 12 may also map the location of a target nerve or other tissue relative to the electrodes connected to one or both of leads 14 and 15 based on the stimulation threshold of each of the electrodes. Information about the relative locations of one or more of electrodes 48 to the target nerve may also be stored in memory 52 or a memory of an external device, e.g., programmer 26. Additionally, in some examples, nerve maps relative to electrodes 48 and/or one or both of leads 14 and 15 may be represented graphically on one or both of clinician programmer 26 and patient programmer 28. Processor 50 of IMD 12 may also be configured to select at least one of electrodes 48 through which to provide stimulation to the nerve or nerves of patient 16 based, at least in part, on the location of the nerve relative to the selected electrode(s). Processor 50 may create a program according to which stimulation may be delivered to patient 16 via the selected electrode(s). The stimulation program may be stored in memory 52 or a memory of an external device, e.g., programmer 26 and may be executed by processor 50 to control stimulation generator 60 to deliver the stimulation to patient 16.

In the example of FIG. 2, electrodes 48A-48P may be implantable and may be deployed on one or more implantable leads. With respect to system 10A of FIG. 1A, leads 14 and 15 may carry electrodes 48A-H and electrodes 48I-P, respectively. In some cases, one or more additional electrodes, such as electrode 48Q, may be located on or within the housing of IMD 12, e.g., to provide a common or ground electrode or a housing anode or cathode. In the example of FIG. 1A, a lead or lead segment carries eight electrodes to provide an 2×8 electrode configuration (two leads with 8 electrodes each), providing a total of sixteen different electrodes. The leads may be detachable from a housing associated with IMD 12, or be fixed to such a housing.

In other examples, different electrode configurations comprising a single lead, two leads, three leads, or more may be provided. In addition, electrode counts on leads may vary and may be the same or different from lead to lead. Examples of other configurations include one lead with eight electrodes (1×8), two leads with four electrodes each (2×4), three leads with four electrodes each (3×4), three leads with eight electrodes each (3×8), three leads with four, eight, and four electrodes, respectively (4-8-4). Additional lead and electrode configurations are also possible and applicable to examples according to this disclosure. In some examples, the lead may be a paddle lead with a number of rows. For example, a paddle lead may have electrodes in any of the configurations above on a single paddle. Different electrodes are selected to form electrode combinations. Polarities may be assigned to the selected electrodes to form electrode configurations.

Electrode 48Q represents one or more electrodes that may be carried on a housing, i.e., can, of IMD 12. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of IMD 12, such as stimulation generator 60, processor 50, memory 52, telemetry module 56, and power source 54.

Wireless telemetry in IMD 12, e.g., with an external programmer, e.g., clinician programmer 26 or patient programmer 28, or another device may be accomplished by radio frequency (RF) communication or proximal inductive interaction of IMD 12 with the external programmer. Telemetry module 56 may send information to and receive information from the external programmer via antenna 65 on a continuous basis, at periodic intervals, at non-periodic intervals, or upon request from the stimulator or programmer. To support RF communication, telemetry module 56 may include appropriate electronic components, such as amplifiers, filters, mixers, encoders, decoders, and the like.

Power source 54 delivers operating power to the components of IMD 12. Power source 54 may include a small rechargeable or non-rechargeable battery and a power generation circuit to produce the operating power. Recharging may be accomplished through proximal inductive interaction between an external charger and an inductive charging coil within IMD 12. In some embodiments, power requirements may be small enough to allow IMD 12 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 12 when needed or desired.

Figure 3:
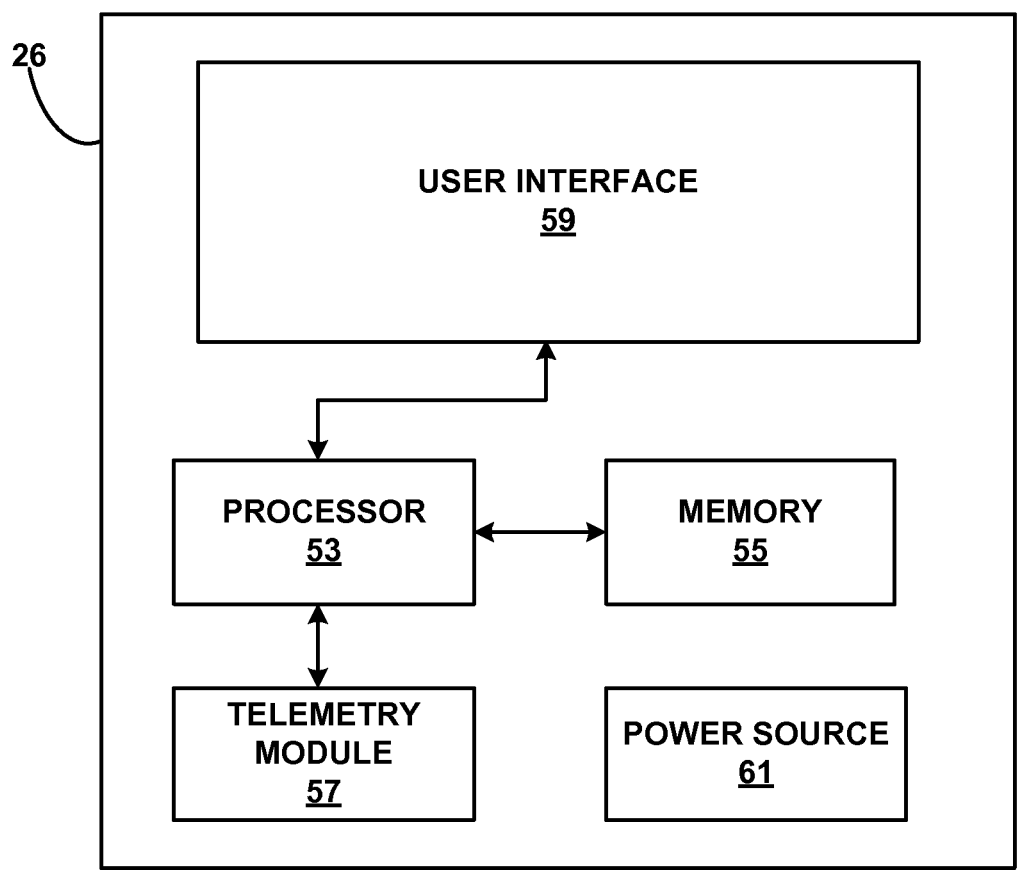
FIG. 3 is a block diagram illustrating various example components of an external programmer for use with an electrical stimulator.

FIG. 3 is a functional block diagram illustrating various components of an external programmer 26 for an implantable stimulator such as IMD 12 (e.g., of FIGS. 1A and 1B). Although the components shown in FIG. 3 are described in reference to clinician programmer 26, some or all of the components may also be included within patient programmer 28 as shown in FIG. 1. As shown in FIG. 3, clinician programmer 26 includes processor 53, memory 55, telemetry module 57, user interface 59, and power source 61. In general, processor 53 controls user interface 59, stores and retrieves data to and from memory 55, and controls transmission of data with IMD 12 through telemetry module 57. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 26 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 26 is used to program therapy for another patient. Memory 55 may also store information that controls operation of IMD 12, such as therapy delivery values.

A clinician or patient 16 interacts with user interface 59 in order to, for example, manually select, change or modify programs, adjust voltage or current amplitude, provide efficacy feedback, or view stimulation data. In some examples, the user interface 59 is used to perform an initial programming protocol according to this disclosure. In the course of the programming protocol or independent of such a process, the clinician or patient 16 may interact with the user interface 59 to indicate occurrence of a stimulation threshold, for example. User interface 59 may include a screen and one or more input buttons that allow external programmer 26 to receive input from a user. In some examples, a clinician interacts with user interface 59 to choose electrodes for stimulation therapy based on a display of the location of the nerve to be stimulated relative to the implanted electrodes 48A-48P. The screen may be a liquid crystal display (LCD), plasma display, dot matrix display, or touch screen. The input buttons may include a touch pad, increase and decrease buttons, emergency shut off button, and other input media needed to control the stimulation therapy. Telemetry module 57 allows the transfer of data to and from IMD 12. Telemetry module 57 may communicate automatically with IMD 12 at a scheduled time or when the telemetry module detects the proximity of the IMD 12. Alternatively, telemetry module 57 may communicate with IMD 12 when signaled by a user through user interface 59. To support RF communication, telemetry module 57 may include appropriate electronic components, such as amplifiers, filters, mixers, encoders, decoders, and the like.

Programmer 26 may communicate wirelessly with IMD 12 using, for example, RF communication or proximal inductive interaction. This wireless communication is possible through the use of telemetry module 57 which may be coupled to an internal antenna or an external antenna. Telemetry module 57 may be similar to telemetry module 56 of IMD 12.

Programmer 26 may also be configured to communicate with another computing device via wireless communication techniques, or direct communication through a wired, e.g., network, connection. Examples of local wireless communication techniques that may be employed to facilitate communication between programmer 26 and another computing device include RF communication based on the 802.11 or Bluetooth specification sets, infrared communication, e.g., based on the IrDA standard.

Power source 61 delivers operating power to the components of programmer 26. Power source 61 may be a rechargeable battery, such as a lithium ion or nickel metal hydride battery. Other rechargeable or conventional batteries may also be used. In some cases, external programmer 26 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Clinician programmer 26 may be used to initiate a programming protocol for IMD 12 in accordance with one or more of the examples described in this disclosure. For example, processor 53 of programmer 26 may communicate with IMD 12 via telemetry module 57 to initiate the delivery of stimulation via electrodes 48 by stimulation generator 60 in a process to determine stimulation thresholds for each of the electrodes 48. Programmer 26 may receive input via user interface 59 from a clinician or patient 16 indicating that a threshold has been reached. In response to such an indication, processor 53 may send a signal to IMD 12 via telemetry module 57 to begin a process of determining which of electrodes 48 is responsible for the threshold, e.g., to control stimulation generator 60 to apply stimulation iteratively at the intensity level at which the patient indicated the threshold occurred for each of electrodes 48 until the electrode that produces the threshold is determined.

Processor 53, memory 55, and other components of programmer 26 may be employed to carry out one or more of the functions described above with reference to processor 50 and memory 52 of IMD 12. For example, processor 53 may be configured to execute instructions stored on memory 55 to map one or more of electrodes 48 relative to a target nerve of patient 16. Processor 53 may also be configured to select candidate electrodes for delivering stimulation based on the location of the selected electrodes relative to the target nerve and create a program including the selected electrodes according to which stimulation generator 60 of IMD 12 may deliver stimulation to patient 16. The stimulation program may be stored in memory 55 of programmer 26 and/or memory 52 of IMD 12.

In some examples, components of IMD 12 may work in conjunction with components of one or both of clinician programmer 26 and patient programmer 28 to program efficacious stimulation parameters and to deliver stimulation therapy to patient 16 in accordance with this disclosure. For example, processor 53 of programmer 26 may control stimulation generator 60 of IMD 12 during a programming session including determining a number of stimulation thresholds and processor 50 of IMD 12 may control stimulation generator 60 to deliver stimulation according to a program including stimulation parameters, e.g., intensity that have been determined based on, among other factors, the stimulation thresholds. Other examples of IMD 12 and one or both of clinician programmer 26 and patient programmer 28 functioning together to program and deliver stimulation therapy to patient 16 in accordance with this disclosure are also contemplated.

Figure 4:
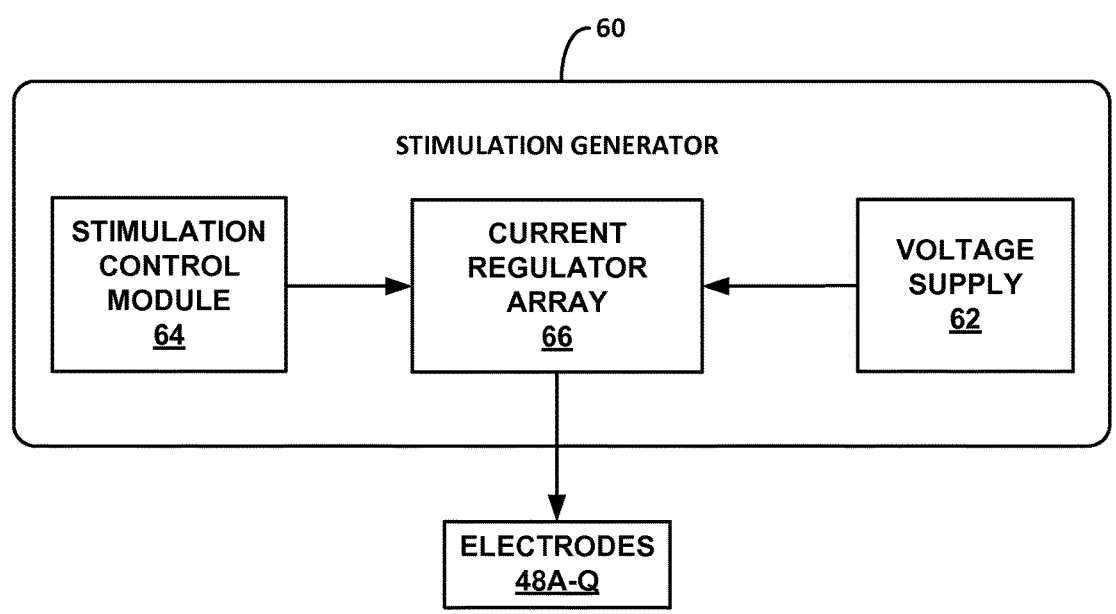
FIG. 4 is a block diagram illustrating various components of an example electrical stimulation generator for use in the implantable electrical stimulator of FIG. 2.

FIG. 4 is a block diagram illustrating various components of an example stimulation generator 60. Stimulation generator 60 may be used with an implantable stimulator, e.g., to perform the functions of stimulation generator 60 as described with reference to FIGS. 1-2. Although described with respect to IMD 12, stimulation generator 60 may also be used for IMD 12, or other types of stimulators. In the example of FIG. 4, stimulation generator 60 is selectively configured, e.g., based on instructions from processor 50 (FIG. 2), to deliver controlled current stimulation pulses to patient 36 via various electrode combinations. In the example illustrated in FIG. 4, stimulation generator 60 includes voltage supply 62, stimulation control module 64, and current regulator array 66.

Voltage supply 62 may receive operating power from power source 54 (FIG. 2). In turn, voltage supply 62 may provide a supply voltage to the current regulators in current regulator array 66. Voltage supply 62 may provide a high supply voltage ($V_{HIGH}$) and a low supply voltage ($V_{LOW}$). The high supply voltage may be coupled to a regulated current source as a supply voltage. The low supply voltage may be coupled to a regulated current sink as a supply voltage. The supply voltage level may be the voltage level used by the current regulator to maintain regulation of the pulse current level. The high and low supply voltages may be positive and negative voltages, respectively, supplied by voltage supply 62. The high supply voltage $V_{HIGH}$ may be used as a high reference voltage level for a current source, and the low supply voltage $V_{LOW}$ may be used as a low reference voltage level for a current sink. As an example, in some implementations, $V_{HIGH}$ may have a voltage level of approximately +12 V to +20 V, and $V_{LOW}$ may have a voltage level of approximately −12 V to −20 V.

Stimulation control module 64 forms a stimulation controller that controls current regulator array 66 to source and sink regulated current stimulation pulses via selected combinations of electrodes 48A-48Q. Stimulation control module 64 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 64 may control delivery of electrical stimulation according to one or more programs that specify stimulation parameters such as electrode combination, electrode polarity, stimulation current pulse amplitude, pulse rate, and/or pulse width. Programs may be defined by a user via an external controller and downloaded to an IMD 12 for use by stimulation control module 64.

Current regulator array 66 includes a plurality of regulated current sources and sinks, each of which may be coupled to a respective electrode. A current regulator may function as either a current source or sink, e.g., by including a source and sink in parallel or by otherwise being selectively configurable to operate as either a source or a sink. For convenience, however, the term "current regulator" may be used in this disclosure to refer generally to either a source or sink. Hence, each of the current regulators in current regulator array 66 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

Each current regulator of current regulator array 66 may be selectively activated to source or sink current via an electrode 48 coupled to the regulator, in which case the electrode is considered active, or deactivated to provide a high impedance connection for the electrode, in which case the electrode may be considered inactive. Hence, each electrode 48 may function as a regulated anode or regulated cathode by connection to a regulated current source or regulated current source, or function as a high impedance node that may not source or sink a significant amount of current. In some examples, stimulation control module 64 selectively activates current regulators in current regulator array 66 to configure electrodes 48 in unipolar, bipolar or multipolar electrode configurations.

In some examples, pulse widths and pulse rates may be selectively controlled by stimulation control module 64 by selectively activating current regulators in current regulator array 66, e.g., on a pulse-by-pulse basis, at selected times and for selected durations. Regulator array 66 may also control the shape of the pulses to control the rise time, overshoot, or overall shape (triangle versus square). In addition, stimulation control module 64 may selectively control individual regulated current sources or sinks in current regulator array 66 to deliver stimulation current pulses via the selected electrodes with desired current levels.

Current regulator array 66 may be used to slowly increase the amount of current to each electrode 48, thereby increasing stimulation intensity during a threshold determination processes. In other examples, current regulator array 66 may be used to provide stimulation at different intensities to different electrodes based on a predetermined relationship. This may be useful, for example, in driving clustered electrodes which have similar usability ranges. Clustering based on usability ranges, as well as determining the relative intensities at which to drive the electrodes is discussed in more detail below with respect to FIG. 16, for example. In some examples, there may be more electrodes than current sources. In such examples, not shown, the stimulation generator 60 may also include a multiplexor to share the sources across multiple electrodes.

Figure 5:
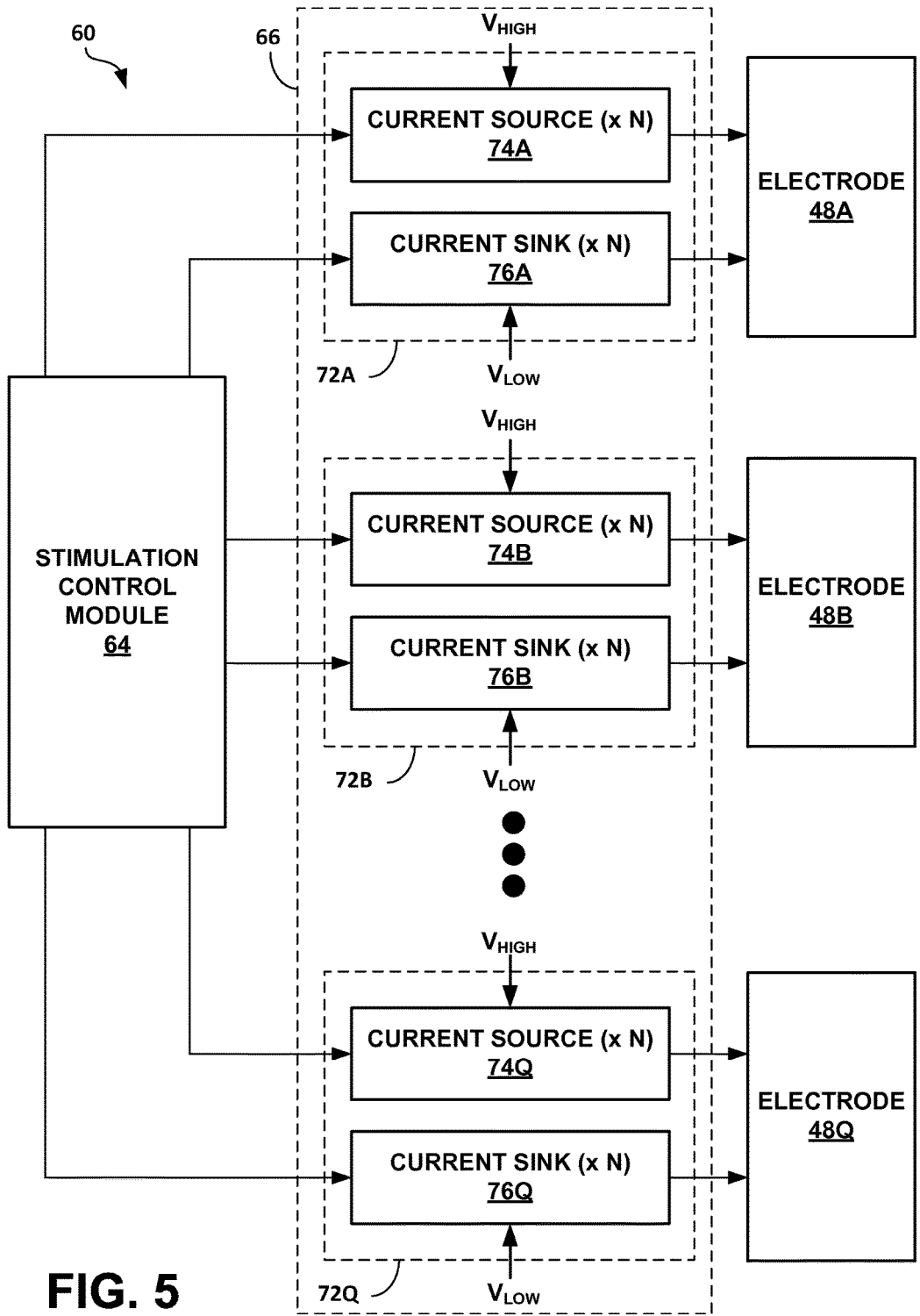
FIG. 5 is a block diagram illustrating the example stimulation generator of FIG. 4 in greater detail.

FIG. 5 is a block diagram illustrating an example of various components of stimulation generator 60 shown in FIG. 4 in greater detail. In particular, FIG. 5 shows current regulator array 66 in greater detail. As shown in FIG. 5, current regulator array 66 includes bidirectional current regulators 72A-72Q. Each of bidirectional current regulators 72A-72Q includes a corresponding one of regulated current sources 74A-74Q that delivers regulated stimulation current to the corresponding electrode and a corresponding one of regulated current sinks 76A-76Q that receives regulated stimulation current from the corresponding electrode.

For electrodes 48 designated as active electrodes in an electrode combination, stimulation control module 64 activates a respective current source 74 or current sink 76 depending on whether the electrode is a cathode or anode. Note that the block diagram illustrated in FIG. 5 is intended as a conceptual diagram that shows how stimulation generator 60 can be configured to control the operation of electrodes 48 in different modes, i.e., a regulated source mode, a regulated sink mode, or an OFF mode (in which both the source and sink may be disabled or disconnected). In other examples, stimulation generator 60 may further include switches to selectively couple some of electrodes 48 to $V_{HIGH}$ or $V_{LOW}$ via unregulated current paths for unregulated modes of operation.

In the example of FIG. 5, current sources 74 may be coupled at one end to the high supply voltage, $V_{HIGH}$, which may correspond to a high reference voltage level of voltage supply 62, and to a corresponding one of electrodes 48 at the other end. Current sinks 76 may be coupled at one end to the low supply voltage, $V_{LOW}$, which may correspond to low reference voltage level voltage supply 62, and to a corresponding one of electrodes 48 at the other end. High voltage ($V_{HIGH}$) and low reference voltage ($V_{LOW}$) represent high and low voltage levels of reference voltage 64 (FIG. 4) and may be supplied by power source 54 (FIG. 2). High voltage $V_{HIGH}$ and low voltage $V_{LOW}$ may be positive and negative voltages, respectively. In other examples, high voltage $V_{HIGH}$ may be a positive voltage and low voltage $V_{LOW}$ may be a ground voltage or other reference voltage.

Stimulation control module 64 controls the operation of regulated current sources 74A-74Q and regulated current sinks 76A-76Q to configure electrodes 48A-48Q as either inactive (i.e., OFF), regulated anodes, or regulated cathodes. For example, stimulation control module 64 may generate control signals to individually control regulated current sources 74A-74Q to deliver specified amounts of regulated current to electrodes 48A-48Q, respectively, and thereby configure such electrodes as regulated anodes. Similarly, stimulation control module 64 may generate control signals to individually control regulated current sinks 76A-76Q to receive specified amounts of regulated currents from electrodes 48A-48Q, respectively, and thereby configure such electrodes as regulated cathodes. For example, stimulation control module 64 may enable the current sources or sinks and also specify control voltages or control currents to be applied to the sources or sinks to control the amount of current that is sourced or sunk via the respective electrodes 48A-48Q. Processor 50 may control stimulation generator 60 to deliver stimulation according to a selected one or more of a plurality of programs or program groups stored in memory 52 such that stimulation current pulses are delivered with desired current levels, pulse rates, and pulse widths. In some examples, processor 50 may control stimulation generator 60 to deliver stimulation according to an initial programming protocol. During the initial programming protocol the intensity of the stimulation delivered to electrodes 48A-48Q may be gradually increased from a base amount. In some examples, the stimulation intensity is increase simultaneously to all electrodes 48A-48Q. In other examples, current sources 74A-74Q may cycle quickly through which of electrodes 48A-48Q is being provided current at a specific level as the overall stimulation intensity increases with each cycle through the electrodes. In some examples, the cycling occurs at a rate that results in a patient perceiving the stimulation as though it is being applied by all electrodes 48 at the same time.

In an example, each current regulator, in the form of either regulated current source 74 or regulated current sink 76, may be implemented as a plurality of regulated current sources and sinks, respectively. The sources operate in parallel to produce a combined, programmable current source level sufficient for a desired stimulation therapy. Similarly, the sinks may operate in parallel with one another to provide a combined current sink level. A regulated current source 74, for example, may be implemented by several parallel regulated current source branches (×N) having identical or similar structures. Similarly, a regulated current sink may be implemented by several parallel regulated current sink branches (×N) having identical or similar structures.

Each individual current source or sink branch may be configured to provide a fixed amount of source or sink current, respectively. In this manner, each current source or sink branch sources or sinks, respectively, a fraction of a total amount of current that can be sourced or sunk by a given current source 74 or current sink 76. A desired current source level for a given electrode 48 may be selected by selectively activating a corresponding number of the N parallel current source branches associated with a current source. Similarly, a desired current sink level for a given electrode 48 may be selected by selectively activating a corresponding number of the N parallel current sink branches associated with a current sink. In this manner, by activating a selected fraction of the parallel current sources or current sinks, a controlled, programmable amount of current may be sourced or sunk via a selected electrode 48.

As an example, each current regulator, e.g., regulated source 74A-74Q or regulated sink 76A-76Q, may be implemented by N parallel current regulator branches. As an example, N may be equal to 64 in some implementations. In this type of implementation, stimulation control module 64 may specify a reference source current and a reference sink current, e.g., based on program data specified automatically or by a user via an external programmer. For each electrode, stimulation control module 64 may further specify a percentage of the reference source current or reference sink current to be delivered via an electrode, e.g., based on program data. For example, stimulation control module 64 may specify that lead electrode 48, configured as an anode, should source 60% of the current to be delivered while lead electrodes 48B and 48C, also configured as anodes, substantially simultaneously source 15% and 25%, respectively, of the current to be delivered. Stimulation control module 64 may also specify that lead electrode 48D, configured as a cathode, and should sink 100% of the current.

A control signal may be applied to each parallel current regulator branch such that the current levels produced by all N branches will add up to approximately the reference current level. Based on the percentage, which may be referred to as a gain ratio, stimulation control module 64 may selectively activate or deactivate a number of parallel current regulator branches for a given electrode sufficient to produce the specified percentage of the reference current. In this manner, stimulation control module 64 selectively scales up or scales down the number of active, parallel current regulator branches used by a given source 74 or sink 76. If the reference current is 20 milliamps (mA), for example, the control signal may be selected such that activation of all N parallel current regulator branches would produce 20 mA of source current or sink current, as applicable, for application via an electrode. In this case, the control signal may be selected such that each of the N current regulator branches produces $1/N^{th}$ of the reference current.

By specifying percentages of source current and sink current for respective electrodes, stimulation control module 64 can control current sources and sinks 74 and 76 to precisely and selectively control the current level sourced by electrodes 48. In addition, the current levels sunk by particular electrodes 48 may also be precisely and selectively control. Further, stimulation control module 64 can support effective shaping of stimulation current to create different electrical stimulation fields or patterns useful in electrical stimulation therapy.

When turned "ON," each parallel current source or sink branch may produce a known amount of current, defined by the reference current and a corresponding control signal, as described above. In this manner, a source branch or sink branch may be considered either ON or OFF, and deliver the same fractional amount of current as other sources or sinks whenever it is ON. Alternatively, in some examples, each parallel current source or sink could be configured to provide different fractional amounts of current, or deliver variable amounts of current according to a bias or control signal. Although it is understood that each given source 74 or sink 76 may include multiple, parallel source branches or sink branches, this disclosure will generally refer to each of sources 74 and sinks 76 on a singular basis for ease of illustration.

Although current levels may be controlled by controlling a number of active current regulator branches as described above, in other examples, current may be controlled alternatively or additionally by directly controlling a current regulator in order to select a variable level of regulated current delivered via the current regulator. Hence, current levels may be controlled by selectively activating parallel current regulator branches with current levels that are set, based on a control signal, to sum to a desired current level, or by directly adjusting the level of current sourced or sunk by a given current regulator.

Although the use of parallel current regulator branches is described for purposes of illustration, either approach could be used. More particularly, in accordance with this disclosure, either approach may be used to control not only the current level sourced or sunk via a current regulator for a given stimulation current pulse, but also to vary the current level during the delivery of a stimulation current pulse. For example, as described in this disclosure, either approach may be used to control the pulse current level to decrease during the pulse width such that a sum of the pulse voltage level and a headroom voltage level of the current regulator does not exceed the supply voltage level, thereby maintaining substantial regulation of the current level.

Figure 6A:
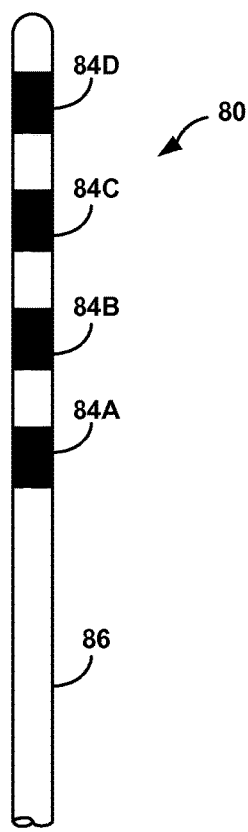
FIGS. 6A and 6B are conceptual diagrams illustrating example leads and electrode configurations that may be used for delivering electrical stimulation therapy.
Figure 6B:
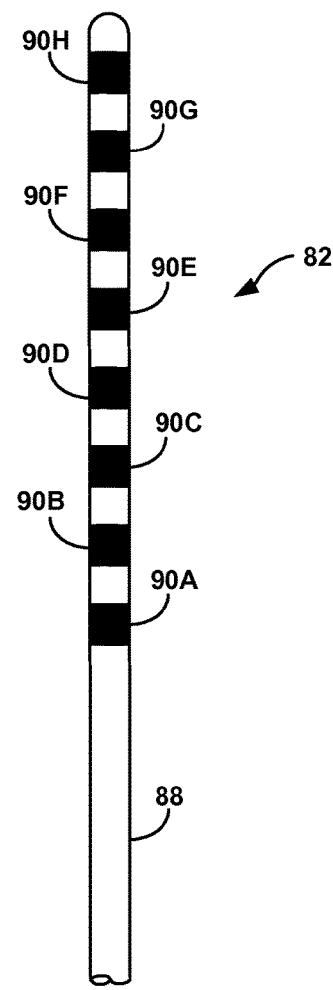

FIGS. 6A and 6B are conceptual diagrams illustrating two different implantable stimulation leads. Leads 80 and 82 are examples of leads 14 and 15 shown in FIG. 1. As shown in FIG. 6A, lead 80 includes four electrodes 84A-84D (collectively "electrodes 84") mounted at various lengths of lead body 86. Lead 82 includes lead body 88, carrying eight electrodes 90A-90H (collectively "electrodes 90"). Electrodes 84A-84D may be equally spaced along the axial length of lead body 86 at different axial positions. Although not depicted, in some examples, each of electrodes 84, 90 may formed by two or more electrode segments located at different angular positions around the circumference of lead body 86 or 88, forming segmented electrodes.

Electrodes of one circumferential location may be lined up on an axis parallel to the longitudinal axis of lead 80 or 82. Alternatively, different electrodes may be staggered around the circumference of lead body 86. In addition, lead 80 or 82 may include asymmetrical electrode locations around the circumference of each lead or electrodes of the same level that have different sizes. These electrodes may include semi-circular electrodes that may or may not be circumferentially aligned. Lead body 86 or 88 may include a radio-opaque stripe (not shown) along the outside of the lead body. Each electrode may be substantially rectangular in shape. Alternatively, the individual electrodes may have alternative shapes, e.g., circular, oval, triangular, or the like.

Figure 7:
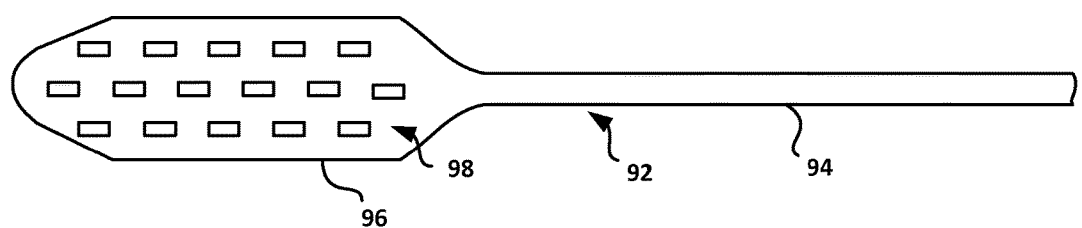
FIG. 7 is a conceptual diagram illustrating an example paddle lead that may be used for delivering electrical stimulation therapy as described in this disclosure.

FIG. 7 is a conceptual diagram illustrating an example paddle lead 92 that additionally or alternatively may be used for delivering electrical stimulation in accordance with the techniques in this disclosure. In the example of FIG. 7, lead 92 includes a lead body 94 and a lead paddle section 96 carrying an array of electrodes 98 arranged in three rows having five, six and five electrodes, respectively. Paddle lead 92 may be configured to include lesser or greater numbers of electrodes. In some implementations, paddle lead 92 may be similar to the Specify™ 5-6-5 paddle lead commercially available from Medtronic, Inc. of Minneapolis, Minn.

Figure 8:
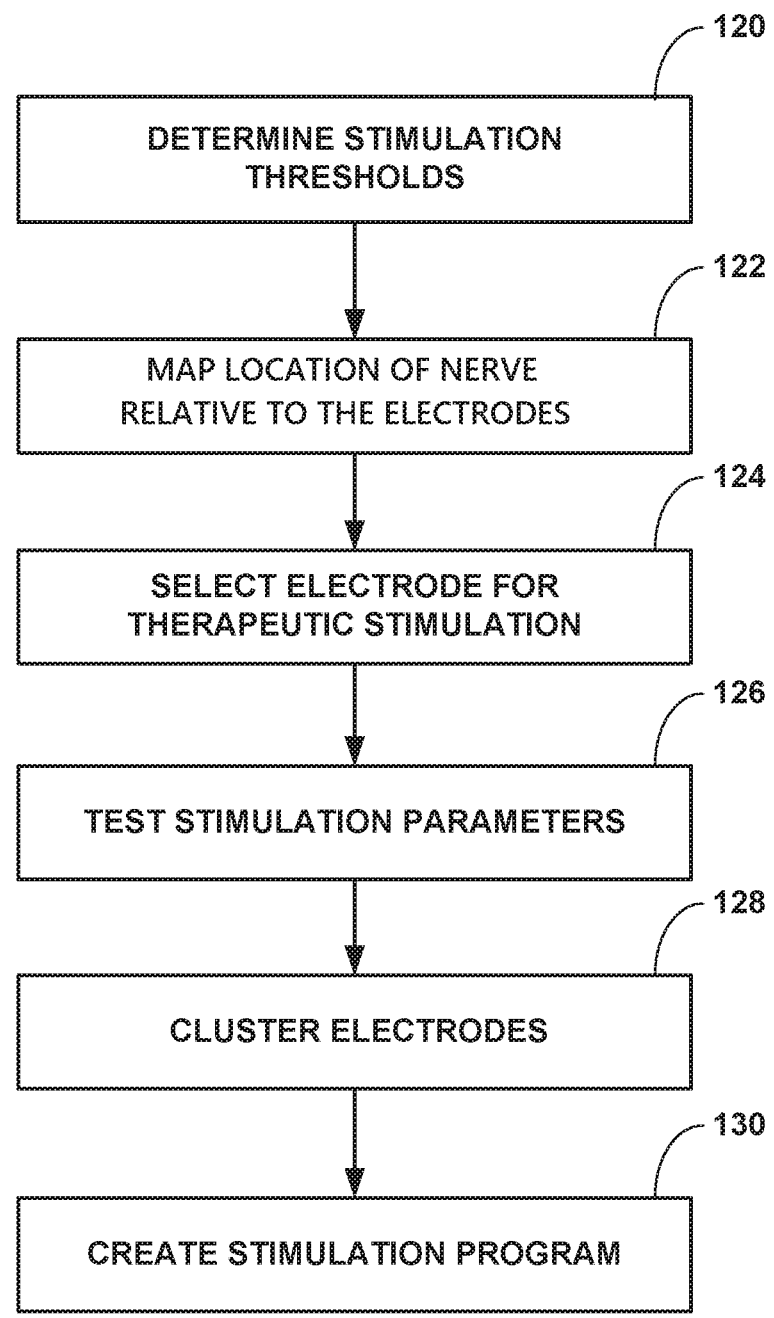
FIG. 8 is a flow diagram illustrating a method for programming an implantable stimulator.

FIG. 8 is a flow diagram illustrating an example method of programming an IMD to deliver stimulation to a patient. The example method of FIG. 8 may be, e.g., part or all of a programming protocol employed by a user, e.g., a clinician to test different electrode combinations and stimulation parameters that may be most efficacious in treating symptoms of a patient's condition. The example method of FIG. 8 includes determining a stimulation threshold for one or more implanted electrodes arranged adjacent nerve tissue (120), mapping a location of the nerve relative to the plurality of electrodes based on the stimulation thresholds of the electrodes (122), selecting an electrode through which to deliver stimulation to the nerve based at least in part on the location of the nerve relative to the selected electrode (124), testing one or more stimulation parameters according to which to deliver stimulation via the selected electrode (126), clustering multiple electrodes including the selected electrode based on at least one stimulation threshold for each of the clustered electrodes (128), and creating a program including one set of stimulation parameters by which stimulation may be delivered via the clustered electrodes (130).

The example method of FIG. 8 includes determining a stimulation threshold for one or more implanted electrodes arranged adjacent nerve tissue (120). As described above, determining one threshold or multiple thresholds for multiple electrodes 48 connected to leads 14 and 15 implanted within patient 16 may be accomplished in a number different ways. In general, however, IMD 12, and, in particular, stimulation generator 60 may be controlled to increase stimulation for one or more of electrodes 48 from a baseline intensity until a first threshold is reached, e.g., until patient 16 indicates feeling a first stimulation threshold. The first threshold may then be used as a new baseline from which to increase stimulation delivered by electrodes 48 until another threshold is reached. This process may be repeated iteratively to determine a number of different stimulation thresholds for one or more of electrodes 48 without ramping stimulation down to zero for each new test. As noted above, in some examples, for each threshold determined based on ramping stimulation delivered by stimulation generator 60 of IMD 12 through one or more of electrodes 48 from a baseline intensity, the particular electrode that produced the stimulation threshold may be identified and associated with the threshold. In one example, the electrode identified as producing and associated with the threshold may be turned OFF and stimulation generator 60 may be controlled, e.g., by processor 50 to increase stimulation from the previously identified threshold for the remaining electrodes 48 that have not been associated with a threshold until a next stimulation threshold is identified. This processor increasing stimulation to a threshold, identifying the electrode that produced the threshold, associating the identified electrode with the threshold, and turning OFF the identified electrode may also be iteratively repeated in the course of determining a number of different stimulation thresholds for electrodes 48.

In some cases, each of electrodes 48 may include multiple stimulation thresholds, including, e.g., one or more lower thresholds like perception and parasthesia thresholds and one or more upper thresholds like muscle recruitment, discomfort, and pain thresholds. In such cases, examples according to this disclosure may be employed to identify all or some of the multiple stimulation thresholds associated with each of electrodes 48. In another example, however, some of electrodes 48 may include only one threshold and some of electrodes 48 may even include no stimulation thresholds. For example, one of electrodes 48 may be so close to a target nerve or an intermediate muscle that the first stimulation threshold that is reached from stimulation delivered by stimulation generator 60 through the electrode is muscle recruitment, discomfort, or pain. In another example, one of electrodes 48 may be located at a distance from a target nerve that is too great to produce any perceivable effects when stimulation is delivered within a prescribed maximum range of stimulation intensities. In any event, examples according to this disclosure may be employed to determine any of a number of different combinations of different stimulation thresholds for any of a number of different combinations of electrodes 48 connected to IMD 12, or other implanted electrodes connected to another implantable stimulator.

Figure 9:
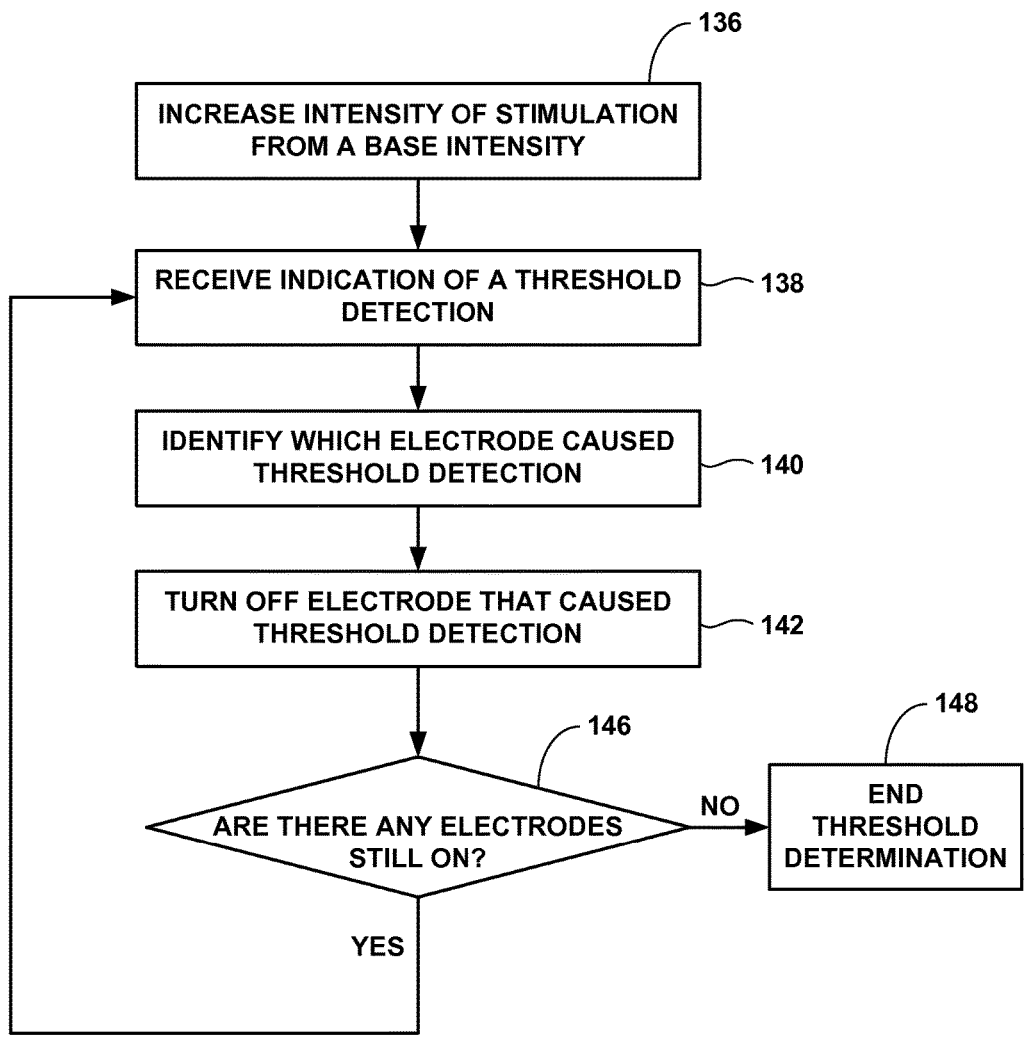
FIG. 9 is a flow diagram illustrating a method of determining a threshold for a number of electrodes.

One example method of determining a stimulation threshold for one or more implanted electrodes arranged adjacent nerve tissue (120) is illustrated in the flow chart of FIG. 9. The method of FIG. 9 includes increasing a stimulation intensity for each of a number of electrodes from a baseline intensity level until a first stimulation threshold is reached (136), receiving an indication that the threshold has been reached (138), identifying a first electrode that produced the first stimulation threshold (140), turning OFF the first electrode that produced the first threshold (142), determining if there are any electrodes that are still ON (146), and, if there are any electrodes still ON, the steps of increasing stimulation intensity from a baseline until a next stimulation threshold is reached (136), receiving an indication that the next threshold has been reached (138), identifying the electrode that produced the next threshold, and turning OFF the identified electrode may then be repeated iteratively until at least one threshold has been identified for each electrode that is capable of producing a stimulation threshold. With each iteration of increasing stimulation intensity from a baseline until the next stimulation threshold is reached, however, instead of starting from the original baseline, e.g., zero, the stimulation may begin from an intensity level that produced one of the previous stimulation thresholds. In some examples, stimulation intensity may be increased from an intensity level that produced the immediately previous stimulation threshold until the next threshold is reached. In some examples, with each iteration after the first stimulation threshold has been determined, stimulation intensity may be increased from an intensity level that produced the first stimulation threshold until the next threshold is reached. The process of determining stimulation thresholds for the electrodes is repeated until it is determined there are not any electrodes that are still ON, after which, the threshold determination method may end or may restart for a different type of threshold. For example, the first time through the method of FIG. 9 a lower threshold, e.g., a perception threshold may be determined for each of a number of electrodes, after which the method may be repeated to determine an upper threshold, e.g., a discomfort threshold for each of the electrodes.

In some examples according to this disclosure, a clinician initiates a threshold determination using programmer 26, e.g., by interacting with user interface 59 of programmer 26. The clinician may tell the patient what type of feeling is associated with the threshold being tested. For example, the clinician may request that patient 16 indicate when the patient first feels any sensation in the region being stimulated. This may be the case when the perception threshold is being determined. In many examples, the perception threshold is the first threshold to be determined for each electrode. In some examples, the paresthesia threshold for each electrode (that has one) is determined. During the determination of paresthesia thresholds, the patient 16 may be asked to indicate when he or she feels a tingling sensation. The tingling sensation may be used to approximate an intensity at and beyond which stimulation may become effective for treatment. In some examples, the threshold determination is conducted to determine the upper level of stimulation tolerable to the patient. In such instances, the patient 16 may be asked to indicate if they feel pain, discomfort or muscle twitching. The patient may also indicate what uncomfortable sensation was felt. In some examples, this upper level of stimulation defines the upper bound or upper threshold of a usability range. As noted above, however, stimulation thresholds for electrodes and the order in which they are reached on a scale of increasing stimulation intensity may vary from implantation location to implantation location, as well as from patient to patient. FIG. 9 is described in the context of determining a perception threshold for each of a number of implanted electrodes, unless otherwise specified. However, the same, or similar, method may be used to determine any of the thresholds associated with each electrode, including determining multiple thresholds for each electrode and a usability range from a lower threshold to an upper threshold for each electrode.

The example method of FIG. 9 includes increasing stimulation intensity for each of a number of electrodes from a baseline intensity level until a first stimulation threshold is reached (136). For example, processor 50 of IMD 12, or processor 53 of programmer 26, may control stimulation generator 60 to increase in the intensity of stimulation delivered to patient 16 via electrodes 48 from a baseline intensity until a stimulation threshold is reached. In some examples, processor 50 controls stimulation generator 60 to increase the stimulation intensity for each of electrodes 48A-48Q at approximately the same time. In some examples, stimulation generator 60 delivers the stimulation via each of electrodes 48A-48Q in quick succession so that the effect of the stimulation is perceived by patient 16 as though stimulation is being applied at the same time. In some examples, stimulation generator 60 increases the stimulation intensity delivered to patient 16 via electrodes 48 by increasing the amplitude of the stimulation signal being applied via the electrodes, e.g., by increasing the voltage or the current amplitude of the stimulation signal. In some examples, stimulation generator 60 increases the stimulation intensity delivered to patient 16 via electrodes 48 by lengthening the pulse width of the stimulation signal being applied via the electrodes. In some examples, the stimulation intensity is increased through a combination of increases in amplitude and pulse width of the signal being applied via the electrodes. Whether to increase amplitude or pulse width in response to a desired stimulation intensity increase may be determined based on which one is more energy efficient for the stimulation generator to deliver, according to previous results from this patient which may favor (or oppose) specific parameter values, or by other means.

The method of FIG. 9 also includes receiving an indication that the threshold has been reached (138). For example, the stimulation intensity delivered by stimulation generator 60 may be increased until programmer 26 receives an indication of threshold detection (138). In some examples, the indication of a threshold may be provided through user interface 59. In some examples, patient 16 may enter that indication of a threshold being reached when the patient first feels stimulation. In some examples the patient may tell the clinician that a threshold has been reached, and the clinician may enter the stimulation intensity level at which stimulation was first perceived. In any event, in one example, programmer 26 may transmit the indication that a threshold has been reached to IMD 12 via telemetry modules 57 and 56, respectively. Processor 50 may control stimulation generator 60 to stop delivering stimulation to patient 16 via one or more of electrodes 48, or, in one example, may control stimulation generator 60 to continue delivering stimulation but to stop increasing the stimulation and maintain the intensity at the level that produced stimulation threshold. In one example, the first threshold reached may be a perception threshold for one of electrodes 48. In some examples, the level of stimulation intensity that resulted in the first perception is stored in memory 55 of programmer 26. In other examples, the level of stimulation intensity that resulted in first perception is transferred to IMD 12 via telemetry module 57 of programmer 26 in communication with telemetry module 56 of IMD 12 and stored on memory 52.

In addition to receiving an indication that the threshold has been reached (138), the method of FIG. 9 includes identifying a first electrode that produced the first stimulation threshold (140). For example, in response to receiving an indication that patient 16 can perceive the stimulation being applied by stimulation generator 60 via electrodes 48, programmer 26 may be employed in conjunction with IMD 12 to determine which of electrodes 48A-48Q caused the threshold detection (140). In one example, programmer 26 may control stimulation generator 60, or instruct processor 50 to control stimulation generator 60 to successively activate each of electrodes 48A-48Q individually at the stimulation intensity that produced the perception threshold until the electrode is identified. In some examples, programmer 26 may direct IMD 12 to turn OFF half of electrodes 48, for example those electrodes on lead 14, and then controls stimulation generator 60 to deliver stimulation via the remaining electrodes to determine whether patient 16 still perceives the stimulation. If patient 16 still perceives the stimulation, then the electrode responsible for the perception is on lead 15. If patient 16 no longer perceives the stimulation, the electrode responsible is on lead 14. The electrode group containing the electrode responsible for stimulation perception may be continually halved until only one electrode is left. In some examples including a paddle lead, e.g., paddle lead 92 of FIG. 7 including more than one row of electrodes, each row of electrodes may be turned on one at a time until the row including the electrode that produces the threshold is identified. After the row including the electrode that produces the threshold is identified, each electrode within the row may be activated one at a time, or the group may be continually halved as described above until the electrode that produces the perception threshold of patient 16 is identified. The programmer 26 then associates the perception level with the identified electrode. In some examples, the stimulation intensity level and electrode may be stored in memory 52 of the IMD 12, e.g., intensity level of and type stimulation threshold and the associated one of electrodes 48 may be stored in a look-up table in a database or other organized aggregation of data in memory 52. In some examples, the stimulation threshold information is stored in memory 55 of external programmer 26.

In some examples according to this disclosure, after the electrode that produces the stimulation threshold has been identified, the electrode may be turned OFF (142). For example, processor 50 may control stimulation generator 60 to deactivate the one of electrodes 48A-48Q that produced the stimulation threshold, e.g., by removing the electrode from the electrodes stimulation generator 60 provides a signal to during subsequent iterations of the method of FIG. 9 to determine additional stimulation thresholds, e.g., additional perception thresholds. Turning OFF electrodes identified as producing a threshold may not be required, in some cases, but it may be difficult for patient 16 to discern additional stimulation thresholds for other electrodes at the same time the previously identified electrode is still producing a perceivable effect.

The method of FIG. 9 also includes determining if there are any electrodes that are still ON (146). In one example, programmer 26 determines if there are any electrodes still on and without associated perception thresholds. For example, programmer 26 may query IMD 12 to determine if any of electrodes 48 are still active for delivering stimulation supplied by stimulation generator 60 to patient 16. In the event none of electrodes are still on, the threshold determination process may stop (148) and may, in some examples, be started over to determine a different type of stimulation threshold, e.g., one of parasthesia, muscle recruitment, discomfort, or pain thresholds for one or more of electrodes 48. If, however, some of electrodes 48 are still on and active for delivering stimulation supplied by stimulation generator 60 to patient 16, programmer 26 may be employed to repeat the steps of increasing stimulation intensity from a baseline until a next stimulation threshold is reached (136), receiving an indication that the next threshold has been reached (138), identifying the electrode that produced the next threshold, and turning OFF the identified electrode may then be repeated iteratively until at least one threshold has been determined for each electrode that is capable of producing a stimulation threshold.

In one example, if one or more of electrodes 48 are still on, signal generator 60 may be controlled, e.g., by processor 50 of IMD 12 of processor 53 of programmer 26, to increase the intensity of stimulation delivered to patient 16 from the remaining active electrodes from the last level of stimulation intensity as baseline until the next stimulation threshold is reached (e.g., repeat step 136). That is, in one example, stimulation generator 60 resumes delivering stimulation to patient 16 at the perception threshold just identified. As explained above, by starting from a level above zero, a significant amount of time may be saved during this initial stage of programming IMD 12. In some examples, (not shown) after the first electrode and perception threshold are identified, the perception threshold for each electrode is determined individually, with the stimulation intensity level starting at the level of the first perception threshold. In some examples, other stimulation thresholds may be determined for each electrode. In some examples, the other stimulation thresholds are determined using a method similar to that used to determine the perception thresholds. However, instead of starting with a base intensity of zero, the base intensity may be the intensity of the lowest perception threshold. In some examples, after the first perception level has been determined, other thresholds for the electrode associated with the first perception level are determined. In one such example, only one electrode may be turned on and capable of delivering stimulation and the stimulation intensity is ramped up from the perception level until it reaches an upper threshold, e.g., a discomfort threshold. Patient 16 may indicate at what intensity the next threshold is experienced, and what type of feeling is associated with the upper level. In some examples, this process may be repeated for all of the other electrodes individually, with the stimulation intensity starting at the perception threshold associated with the first electrode.

Although the foregoing example described with reference to the method of FIG. 9 included determining perception thresholds for each of electrodes 48 (capable of producing a perception threshold) implanted within patient 16, in some examples, threshold determinations according to this disclosure may include determining a lower and an upper threshold and a usability ranged defined thereby for each of a number of electrodes implanted within a patient. Additionally, referring again to the example method of FIG. 8, the step of determining a stimulation threshold for one or more implanted electrodes arranged adjacent nerve tissue (120) may include determining a lower and an upper threshold and a usability ranged defined thereby for each of a number of electrodes implanted within a patient, one or more of which values may be employed in the method of programming of FIG. 8 or other such methods in accordance with this disclosure.

In one example, programming may begin with a determination of a lower threshold for each of electrodes 48 connected to leads 14 and 15 implanted within patient 16. In some examples, as explained above with respect to FIG. 9, the lower threshold is determined through an iterative process. For example, the stimulation intensity provided to each of electrodes 48 is slowly increased by stimulation generator 60 until patient 16 provides an indication that stimulation is felt. As explained above with reference to FIG. 9, the steps of increasing stimulation intensity from a baseline until a next stimulation threshold is reached, receiving an indication that the next threshold has been reached, identifying the electrode that produced the next threshold, and turning OFF the identified electrode may be repeated iteratively until a lower threshold has been determined for each electrode that is capable of producing such a threshold.

After the low threshold has been determined for each of electrodes 48 of IMD 12, an upper threshold for each electrode may be determined. In some examples the upper threshold is a pain threshold. In some examples, the upper threshold is a discomfort threshold. In some examples, the upper threshold is determined by stimulation generator 60 slowly increasing the stimulation intensity level from a base level. In some examples, the base level is the first detected lower threshold. The upper thresholds for electrodes 48 may be determined in a similar manner as described above with reference to lower thresholds and as described in detail with reference to the example method of FIG. 9.

In some examples, programmer 26, e.g., processor 53 of programmer 26 may be configured to determine a usability range for each of electrodes 48 (124) based on information stored in memory 52 or memory 55 regarding the upper and lower thresholds for each electrode. In general, an electrode's usability range is the range of stimulation intensities between an identified lower threshold and an identified upper threshold. In some examples, the usability range is from the perception threshold to an upper threshold such as the pain threshold. In other examples, the usability range is from the paresthesia threshold to an upper threshold. Defining usability ranges for electrodes 48 or combinations of electrodes 48 by which stimulation will be delivered to patient 16 by stimulation generator 60 may assist in programming by narrowing the range of possible stimulation intensities that may produce efficacious stimulation therapy to the patient. For example, by defining a usability range between a perception and a pain threshold of patient 16 for a particular one of electrodes 48 or combination of electrodes 48, testing within that range may result in stimulation intensities that are high enough to produce perceivable effects but not too high so as to produce undesirable side effects, such as pain. In some examples, instead of a single stimulation threshold, multiple thresholds such as the usability range may be employed for different reasons in examples according to this disclosure. For example, the usability range of electrodes 48 may be employed to map the location of a nerve relative to the electrodes or to cluster individual electrodes or combinations of electrodes together for stimulation delivery, as described below in more detail.

In some examples, a usability range may be defined as the range from a first positive outcome, such as pain relief, to the highest tolerable level of stimulation. In other examples, a range may be established between two different undesirable outcomes. For example, between an uncomfortable intensity and pain or muscle recruitment. The range may be defined by the first stimulation threshold registered and the point where the stimulation intensity becomes unbearable. This type of usability range may be used for mapping or for other purposes even though the range is not useful for therapeutic purposes, and the electrode or electrode combination may not be used to provide stimulation therapy.

Referring again to FIG. 8, in addition to determining a stimulation threshold for one or more implanted electrodes arranged adjacent nerve tissue (120), the example method includes mapping a location of a target nerve relative to a number of electrodes based on the stimulation thresholds of the electrodes (122). In some examples, based on at least the lower threshold for each of electrodes 48, programmer 26 and/or IMD 12 may map the location of the nerve relative to the electrodes. In other examples, however, multiple thresholds, including, e.g., usability ranges including lower and upper thresholds for electrodes 48 may be employed by processor 53 of programmer 26, or processor 50 of IMD 12, to map the location of the target nerve of patient 16 relative to the implanted electrodes. In some cases, the intensity level at which a stimulation threshold is produced an increasing function of the distance between the electrode or electrode combination producing the threshold and the nerve at which the stimulation is directed. As such, the lower the stimulation intensity at which the threshold (e.g., perception or paresthesia) is produced, the closer the electrode that produces the threshold is to the nerve being stimulated. Based on the relative values of the lower threshold, as well as the rate of increase in the lower threshold in the electrodes surrounding the electrode(s) determined to be the closest to the nerve, an estimate may be made regarding the general direction and location of the nerve relative to the electrodes. In some examples, with a single lead crossing the nerve, the lower thresholds increase by the same amount on both sides of the electrode with the lowest threshold. This may indicate that the electrode is at a ninety degree angle to the nerve. In some examples, a paddle lead or multiple leads may be employed to deliver stimulation. In such examples, the mapping of the electrodes relative to the nerve being stimulated may provide a more in depth picture of the relative locations of each, e.g., in multiple dimensions rather than a single dimension in the case a row of electrodes is arranged generally transverse to a nerve. In some examples, information from the upper threshold, such as muscle recruitment, may provide information that can be used to determine the relative location of other nerves in the area as well. For example, if a particular electrode has an upper threshold that is a muscle recruitment threshold, then a nerve innervating the muscle tissue may be between the target nerve and the electrode. The process of mapping the relative location of electrodes and the stimulated nerve is discussed in more detail below with respect to FIG. 10.

Figure 10:
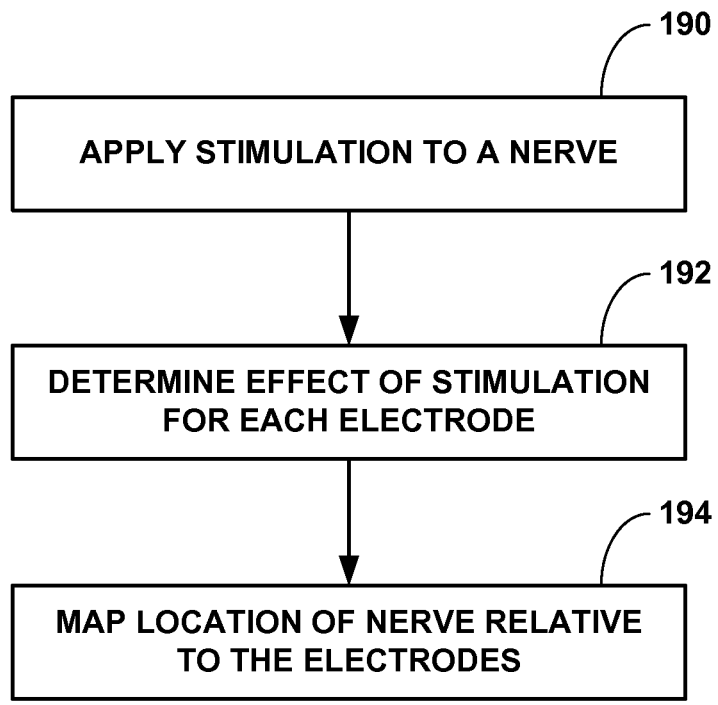
FIG. 10 is a flow diagram illustrating a method of determining the location of a nerve in relation to a number of implantable electrodes.

FIG. 10 is a flow diagram illustrating a method of determining the location of a nerve in relation to one or more implantable electrodes. The example method of FIG. 10 includes applying stimulation to a nerve via each of a number of implantable electrodes arranged proximate to the nerve (190), determining an effect of the stimulation for each of the electrodes (192), and mapping a location of the nerve relative to the electrodes based on the effect of the stimulation for each of the electrodes (194). The steps of applying stimulation and determining the effects of stimulation may be executed in a similar manner as described above with reference to FIGS. 8 and 9 regarding determining one or more stimulation thresholds for each of electrodes 48.

In one example, the determination of the relative location of the nerve being stimulated to electrodes 48 may include applying stimulation to the nerve via each of electrodes 48. In some examples, the electrodes may be connected to a paddle lead, e.g., paddle lead 92 of FIG. 7. In some examples, the lead may include a single row of electrodes implanted in a location, and with an orientation that is believed to be generally transverse with respect to the target nerve, e.g., one or more occipital nerves, e.g., one of leads 80 or 82 of FIGS. 6A and 6B, respectively. In one example, programmer 26 may determine the effect of the applied stimulation for each electrode. In some examples, the determination of the effect of the stimulation includes determining a perception or other stimulation threshold value for each of the electrodes 48 using the method discussed above with respect to FIG. 9. Based on the perception or other stimulation thresholds, programmer 26, and, in particular, processor 53 of programmer 26 may map the location of the nerve relative to electrodes 48. In some examples, this includes determining which electrodes have the lowest perception levels. The lower the perception level, the closer to the nerve the electrode is located. Based on the relative values of each perception level, programmer 26 may also determine the direction the nerve extends from the electrode(s) with the lowest perception level. The process of mapping a nerve relative to a number of electrodes is explained in greater detail with reference to the stimulation threshold graphs of FIGS. 11 and 12, which are respectively directed to mapping the location of a nerve relative to a single row of electrodes arranged generally transverse to the nerve and to mapping the location of a nerve relative to multiple rows of electrodes, e.g., on a paddle lead or multiple single row leads arranged generally transverse to the nerve.

Figure 11:
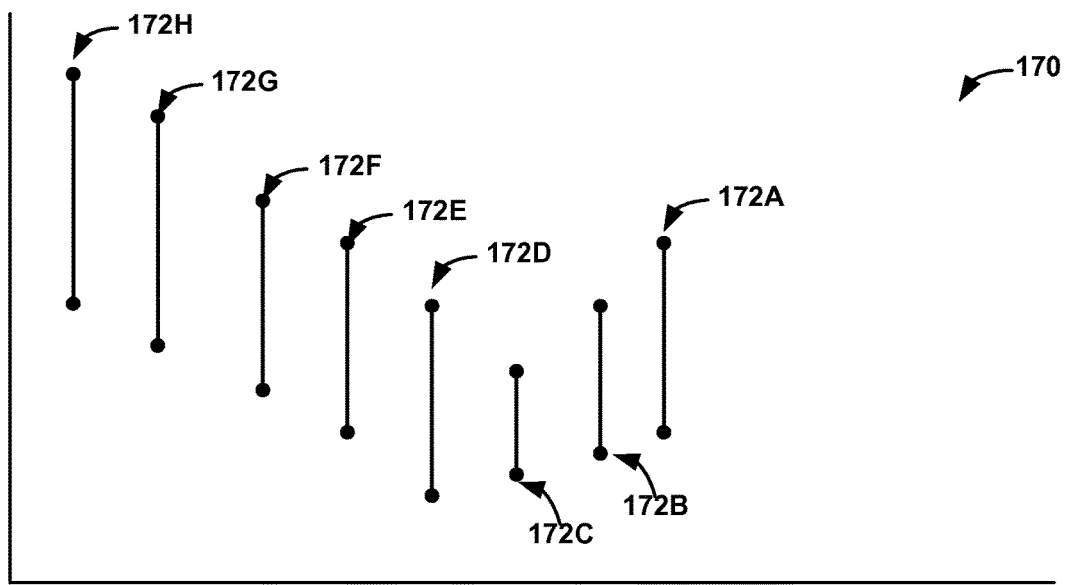
FIG. 11 is a graph illustrating usability ranges including lower and upper stimulation thresholds for a number of electrodes connected to an implantable stimulation lead.
Figure 11:
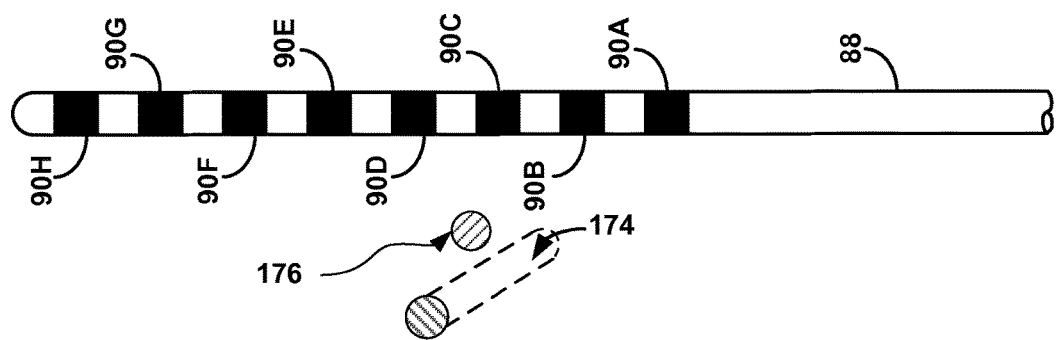

FIG. 11 is a graph illustrating usability ranges including lower and upper stimulation thresholds for a number of electrodes connected to an implantable stimulation lead. FIG. 11 is described with reference to lead 88 including electrodes 90A-90H. In FIG. 11, graph 170 shows the usability ranges 172A-172H of electrodes 90A-90H of lead 88, respectively. The lower perception level of usability range 172D, in comparison to the other usability ranges 172A-172C and 172E-172h, indicates that electrode 90D is closest to nerve 174 being stimulated in the example of FIG. 11. In addition, the relatively shorter increase between the perception threshold of 172C and 172 D as compared to the increase in perception threshold between 172D and 172 E indicates that the nerve is in a direction tending towards electrode 90C. Information collected regarding each electrode may provide information in addition to the approximate location of the nerve with respect to the electrodes 90A-90H. For example the shorter usability range of electrode 90C, coupled with information from the patient that the upper end of usability range 172C is a result of muscle recruitment, may indicate that an additional nerve 176 is between lead 88, and in particular electrode 90C, and the nerve 174 the IMD 12 was implanted to stimulate.

The example of FIG. 11 illustrates the manner in which a location of a nerve may be mapped relative to a number of electrodes based on the effect of the stimulation for each of the electrodes on the nerve (194) in accordance with the example method of FIG. 10. In particular, FIG. 11 illustrates the manner in which the location of nerve 174, which may be, e.g., an occipital nerve of patient 16, is mapped relative to electrodes 90A-90H on lead 88 based on usability ranges 172A-172H of the electrodes, each of which includes a lower and an upper stimulation threshold representing different effects of stimulation delivered by the electrodes to patient 16.

Figure 12:
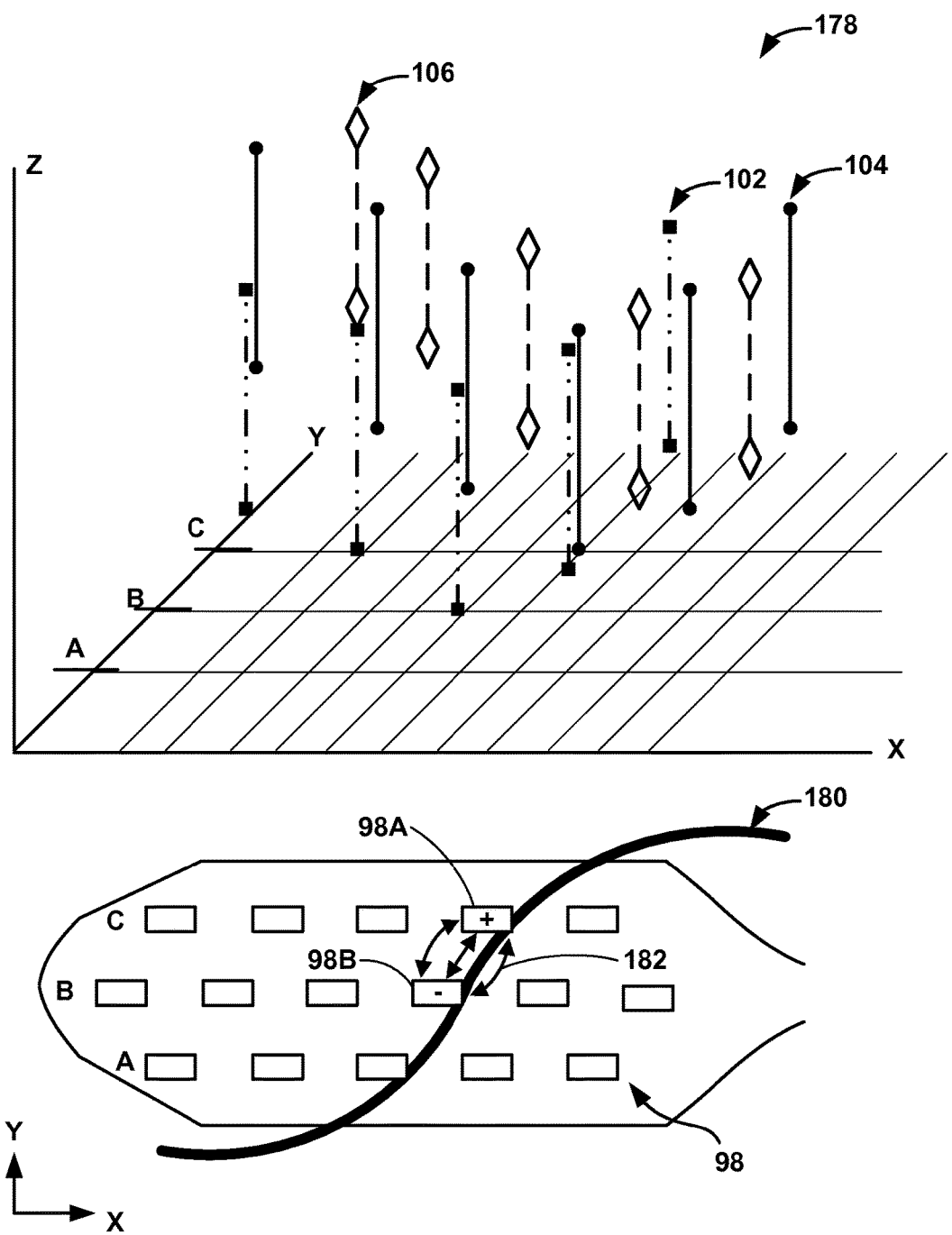
FIG. 12 is a graph illustrating usability ranges including lower and upper stimulation thresholds for a number of electrodes arranged in a number of rows on an implantable paddle lead.

FIG. 12 is a graph illustrating usability ranges including lower and upper stimulation thresholds for a number of electrodes arranged in a number of rows on an implantable paddle lead. FIG. 12 is described with reference to a paddle lead including electrode array 98. Electrode array 98 includes three rows of electrodes, A, B and C. Graph 178 includes usability ranges for each of the electrodes of array 98. The Z axis of Graph 178 is intensity. The X and Y axis are equivalent to a plane in which paddle lead 88 lies or to which paddle lead 88 is parallel. Accordingly, the grid along the X-Y plan corresponds to the plane of the paddle lead 88, and electrode array 98. The usability ranges 102 are for electrodes in row A. The usability ranges 104 are for electrodes in row B, and the usability ranges 106 are for electrodes in row C. As shown, nerve 180 runs below three electrodes, one in each row. Each of those electrodes is depicted as having the lowest perception threshold of the electrodes in their respective rows. In a similar manner as described with reference to the example of FIG. 11, the location of nerve 180 may be mapped relative to the electrodes in array 98 employing the usability ranges of each of the electrodes. In the example of FIG. 12, however, the mapping may include information in multiple dimensions. For example, nerve 180 in FIG. 12 is mapped in two dimensions, X and Y, relative to electrodes of array 98. The X and Y dimensions are oriented parallel to the paddle lead 88. Mapping nerve 180 in multiple dimensions relative to electrodes of array 98 may have additional benefits with respect to programming an IMD, e.g., IMD 12 to deliver stimulation via the electrodes. In some examples, stimulation directed at a nerve may be more efficacious when the direction of the stimulation is generally parallel to the nerve. In the example of FIG. 12, because nerve 180 has been mapped in two dimensions relative to electrodes of array 98, it may be possible to select electrodes or electrode combinations that will produce stimulation in a particular direction, e.g., in a direction parallel to nerve 180. For example, a bipolar combination of electrodes 98A and 98B may be selected for delivering stimulation to nerve 180, because the direction of stimulation produced by the combination of electrodes 98A and 98B may be generally parallel to nerve 180, as illustrated by stimulation field lines 182 in FIG. 12. In some examples, the electrodes of array 98 may be activated to produce an electrical stimulation field of a particular shape. For example, more complex combinations of electrodes in array 98 than a monopole or bipole may be selected to produce stimulation fields of varying sizes, shapes, and that emanate from the electrodes, or, in other words, are steered in different directions from the selected electrodes. Different stimulation parameters, including amplitude, pulse width, and frequency may also be employed in such electrode combinations to tailor the shape, size and direction of the field produced by the electrodes of array 98 selected for stimulation. In this manner, electrical stimulation may be delivered in a specific direction from and in a manner to cover a specific volume adjacent lead 88 to enhance therapy efficacy and reduce possible adverse side effects from stimulating a large volume of tissue. Mapping nerves relative to implanted electrodes may have this and other benefits in examples according to this disclosure, as described in more detail with reference to FIG. 13.

In some examples, not shown in FIG. 12, a variety of map types are possible from the data collected regarding the various stimulation thresholds for each electrode. For example, processor 50 of IMD 12 or processor 53 of external programmer 26 may generate a heat map, or a two or three-dimensional contour map using shapes or colors to specify the type of threshold achieved. For example, different colors may be used to depict a muscle recruitment threshold versus a pain threshold or a discomfort threshold. In some examples, processors 50 or processor 53 also maps the paresthesia area for each electrode that has a paresthesia threshold. The paresthesia area may be used to determine if an electrode stimulates more than one nerve or nerve branch or the amount of tissue activated by the electrode, for example. In some examples, the paresthesia area may indicate what portion of the nerve the stimulation from a given electrode reaches at a level that may provide paresthesia effects.

Referring again to FIG. 8, in addition to mapping a location of a target nerve relative to a number of electrodes based on the stimulation thresholds of the electrodes (122), the example method of FIG. 8 includes selecting an electrode through which to deliver stimulation to the nerve based at least in part on the location of the nerve relative to the selected electrode (124). In examples according to this disclosure, electrodes may be selected for stimulation delivery based on one or more stimulation thresholds. In some examples, electrodes may be selected as a byproduct of nerve mapping, which is based on stimulation thresholds.

Figure 13:
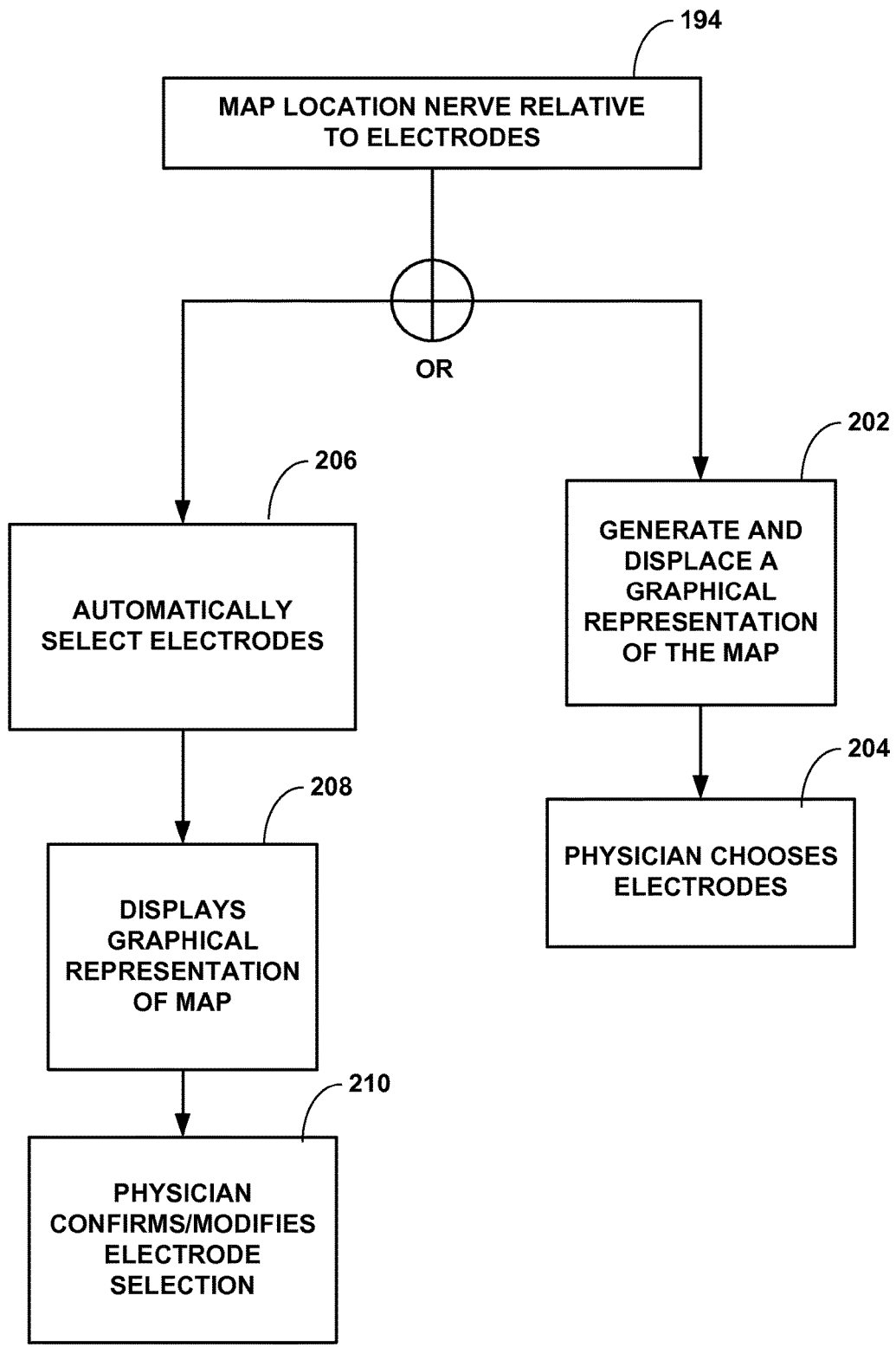
FIG. 13 is a flow diagram illustrating a method of selecting electrodes to provide stimulation therapy to a patient.

For example, FIG. 13 is a flow diagram illustrating different functions that may be executed as a result of nerve mapping according to this disclosure, including selecting electrodes for stimulation based on the nerve map and/or graphically representing the nerve map to a user, e.g., on an external programmer or another external device. In general, the electrodes that are most useful for providing electrical stimulation are those closest to the nerve being stimulated or which are oriented preferentially (parallel vs. orthogonal) to the nerve being stimulated. Accordingly, the first step in choosing electrodes may be to map the relative location of electrode and the nerve(s) (194) to be stimulated, as described above with reference to the example nerve mapping method of FIG. 10. After the mapping, electrode selection may occur in one of two ways.

In one method, programmer 26 or IMD 12, e.g., processor 53 of programmer 26 or processor 50 of IMD 12 may automatically select electrodes (206) as potential candidates for delivering stimulation therapy to patient 16. The automatic selection may be based on some predetermined criteria stored in memory 55 or memory 52 and executable by one or both of processors 53 and 50 of programmer 26 and IMD 12, respectively. In some examples, the criteria may include electrodes that are close to the nerve, or bipolar groupings of electrodes that result in a bipole parallel to the nerve, for example as described above with reference to electrodes 98A and 98B and nerve 180 in FIG. 12. In some examples, two or more electrodes may be chosen and activated together in accordance to a set of stimulation parameters configured to provide an electrical stimulation field of a particular size, shape, and direction. Programmer 26 may also display, e.g., on user interface 59, a graphical representation of the map (208) of the relative locations of the electrodes and nerve(s). In some examples, the graphical representation of the map may include representations of the direction of voltage or current flows resulting from a chosen electrode combination. Such representations displayed by programmer 26 may include predicted visualizations of the electric field, current density, or voltage gradient. In some examples, the automatically selected electrodes are highlighted or otherwise emphasized or indicated to a user on the graphical display of user interface 59 of programmer 26. A user, e.g., a clinician may confirm or modify the automatic electrode selection (210) employing programmer 26 based, at least in part, on the graphical representation. In some examples, other information, including patient feedback to stimulation provided by the selected electrodes may also affect the choice of electrodes.

In another example, programmer 26 may generate a graphical representation of the map of the location of the nerve relative to the electrodes (202). For example, processor 53 of programmer 26 may generate a representation of the nerve map and control a display of user interface 59 to display the representation. Based on the graphical representation, a clinician may chose electrodes (204) to provide stimulation therapy to patient 16. The selection may be based on the type of stimulation to be provided, the relative location of the electrodes and nerves, or the direction of stimulation provided by an electrode or combination of electrodes, for example.

Referring again to FIG. 8, the example method also includes testing one or more stimulation parameters according to which to deliver stimulation via the selected electrodes or electrode combinations (126). As a result of the threshold determinations and nerve mapping methods according to this disclosure, a number of electrodes and/or electrode combinations are selected as configured to deliver efficacious therapy to patient 16. During this process, the stimulation parameters by which thresholds are determined and selected electrodes are tested may be held generally constant, except for, e.g., stimulation intensity. For example, a default set pulse width and frequency may be used throughout this process. After efficacious electrodes and electrode combinations have been selected based on the stimulation thresholds and nerve mapping, however, stimulation parameters, including, e.g., amplitude, pulse width, and frequency may be tested for each of the selected electrodes and electrode combinations to further improve the efficacy of stimulation delivered thereby.

Referring to the example IMD 12 of FIG. 2, programmer 26 may be employed, e.g., by a clinician and/or patient 16 to control stimulation generator 60 to delivery therapy via different ones and/or combinations of electrodes 48A-48Q selected as a result of the foregoing threshold determinations and nerve mapping. In particular, signals received from programmer 26, for example, may cause processor 50 to modify one or more stimulation parameters used to deliver stimulation therapy via the selected electrodes and/or electrode combinations to test different potentially efficacious stimulation programs including an electrode or combination and particular stimulation parameter values. Stimulation parameters may be tested within a range of values that may be known to be appropriate for particular nerves and/or conditions. An exemplary range of electrical stimulation parameters likely to be effective in treating the effects of symptoms of a chronic condition related to one or more cranial nerves of patient 16, e.g., pain associated with migraine headaches or occipital or trigeminal neuralgia, are listed below. In some examples, programmer 26 may be employed to control stimulation generator 60 to deliver stimulation to patient 16 to test pulse rate/frequency, amplitude, and width within the following ranges.

1. Pulse Rate/frequency: between approximately 4 Hz and approximately 1200 Hz, more preferably between approximately 4 Hz and approximately 130 Hz, and still more preferably between approximately 40 Hz and approximately 80 Hz.

2. Amplitude: between approximately 0.1 volts and approximately 10.5 volts. In other examples, a current amplitude may be specified or measured in terms of the voltage that is delivered. For example, the range of current amplitude may be between approximately 0.1 milliamps (mA) and approximately 20 mA.

3. Pulse Width: between approximately 10 microseconds and approximately 1000 microseconds, more preferably between approximately 50 microseconds and approximately 400 microseconds.

Depending on the application, different ranges of parameter values may be used by IMD 12, and, in particular, generator 60 to deliver stimulation via one or more of electrodes 48 on leads 14 and/15 to patient 16.

As noted above, one of the stimulation parameters that may be tested to improve efficacy is pulse width. Pulse width, in addition to amplitude, contributes to stimulation intensity. Thus, in the course of stimulation threshold determinations, one or both of amplitude and pulse width may be modified to vary stimulation intensity in order to determine one or more stimulation thresholds. Another effect of varying pulse widths is that it may modify the stimulation thresholds and usability range of an electrode through which stimulation is delivered at a given amplitude with the varying pulse widths. Thus, by manipulating pulse widths, for example, usability ranges may be increased or decreased and the entire range including a lower and an upper stimulation threshold may be shifted up or down the stimulation intensity scale. In this manner, to some degree, varying pulse widths may be employed to modulate stimulation thresholds and usability ranges for various electrodes implanted within a patient. Such adjustments to thresholds and usability ranges may be employed for a number of different reasons, including, e.g., improving existing electrode clusters or expanding the number of electrode clusters that may be created and through which stimulation may be delivered to a patient.

Figure 14:
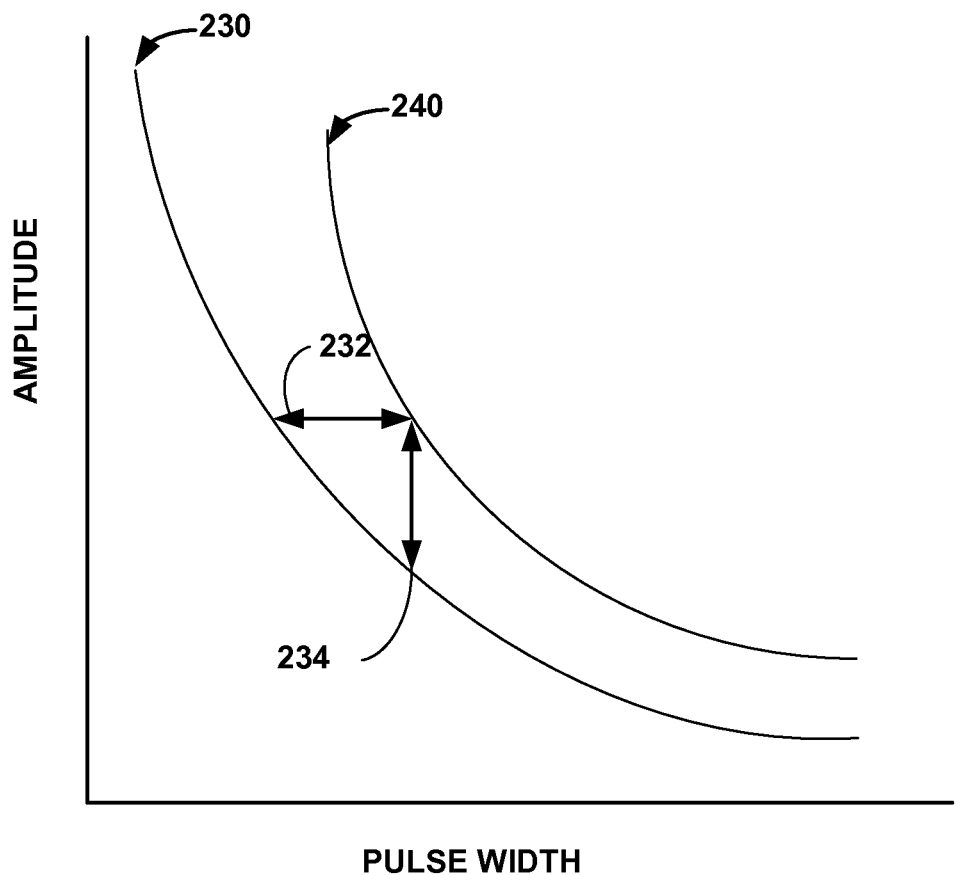
FIG. 14 is a graph illustrating the relationship between stimulation thresholds, pulse width, and amplitude.

FIG. 14 is a graph illustrating the relationship between stimulation thresholds, pulse width, and amplitude. Curve 230 represents an example paresthesia threshold curve as a function of amplitude and pulse width. Curve 240 represents an example of a curve for a different diameter nerve fiber, one which may relate to pain/discomfort threshold curves, as a function of amplitude and pulse width. Stimulation intensity is a function of the combination of both amplitude of the pulse being applied as well as the pulse width. By varying either the amplitude or the pulse width, changes in the usability range of the other factor may be achieved. For example, arrow 232 illustrates the usability range for pulse width at a given amplitude. Arrow 234 represents a usability range based on amplitude for a give pulse width. During parameter optimization it may be beneficial to modify either amplitude or pulse width to maximize the distance between comfort and pain, or, in other words, to increase the usability range between a lower stimulation threshold and an upper threshold. Additionally, if the two curves (230, 240) are results of two different fiber types or different fiber diameters, then stimulating at different points on the curves may allow selectivity with respect to the different outcomes afforded by the different nerve fibers. Depending on whether amplitude or pulse width is being modulated during stimulation therapy, the other parameter may be changed to provide an improved usability range of the other. In some examples, the choice of which usability range, i.e. pulse width or amplitude, to test and improve may be based, at least in part, on which the patient appears to respond to the most. As noted above, adjusting stimulation thresholds and usability ranges may be used for other reasons, including, e.g., improving electrode clustering according to this disclosure.

In addition to testing one or more stimulation parameters according to which to deliver stimulation via the selected electrodes or electrode combinations (126), the example method of FIG. 8 includes clustering multiple electrodes including the selected electrode based on at least one stimulation threshold for each of the clustered electrodes (128). Clustering electrodes is different than grouping electrodes into an electrode combination in a stimulation program according to which to deliver stimulation to a patient. Clustering electrodes is also different than delivering stimulation via multiple stimulation programs (e.g., including multiple electrode combinations configured according to multiple sets of stimulation parameters) simultaneously. Clustering electrodes may refer to grouping multiple individual electrodes and/or electrode combinations that have been determined to be generally efficacious and configuring the multiple electrodes and/or electrode combinations to deliver stimulation as part of one program. Clustering electrodes may be useful in situations where device configuration limits the number or type of stimulation programs that may be employed. For example, in some implementations of an implantable neurostimulator, the number of distinct stimulation programs that may define stimulation delivered to a patient may be limited to a number that is less than the number of different efficacious electrode combinations by which stimulation may be delivered to a particular patient. In such circumstances, clustering multiple electrode combinations in a single program may increase resource utilization and may ultimately improve the efficacy of the therapy delivered to the patient. Clustering may also be advantageous to minimize the complexity of the system that a patient is asked to manage. For instance, often each program is available to a patient for adjustment and control. In this case, the fewer programs afforded by clustering similar electrodes may mean a more easy to use, less complex system.

Clustering may include determining if one or more electrodes have similar characteristics that allow for stimulation to be provided to a nerve using the electrodes configured to deliver stimulation according to the same stimulation program, e.g., according to the same stimulation parameters including, e.g., intensity, pulse width, and frequency. In some examples, electrodes may be clustered based on one or more stimulation thresholds associated with each of the electrodes or combinations thereof for a particular patient. For example, electrodes with similar paresthesia thresholds may be clustered together. In another example, electrodes or combinations of electrodes with similar usability ranges, e.g., similar low and/or high thresholds and similar ranges of stimulation intensities may be clustered together.

Clusters may be formed that include electrodes before an upper threshold is reached. All electrodes that cause muscle recruitment may be grouped together. Electrodes may also be clustered based on whether they produce paresthesia in a given region, e.g., a particular volume of tissue within the patient. In general, electrodes may, in some examples, be clustered based on the outcome(s) of stimulation delivered therefrom, rather than only by threshold values.

Clustering may also include determining whether, in addition to similar characteristics, electrodes may have desired differing characteristics. In some examples, electrode clustering may include choosing electrodes that have similar stimulation thresholds, but may stimulate different nerve targets. For example, an electrode that stimulates the left occipital nerve may be clustered with an electrode that stimulates the right occipital nerve based on similar stimulation thresholds. In some examples, electrodes with similar thresholds may be clustered based on non-overlapping paresthesia areas.

In one example, programmer 26 may be employed to cluster multiple electrodes 48 or combinations thereof based on the lower threshold of each electrode stored in memory 55 of programmer 26 and/or memory 52 of IMD 12, for example. Electrodes with similar perception or paresthesia threshold may be clustered for use with the same stimulation program. In some examples, an initial clustering based on lower threshold values may be further pruned or declustered to include only those electrodes or combinations of electrodes with both similar lower thresholds and similar upper thresholds, which, in turn, equates to similar usability ranges. This allows for stimulation to be provided by a single stimulation generator to all electrodes in the cluster. In some examples, clustering provides some additive effect or benefit from the activation of a plurality of electrodes over a single electrode being activated alone. This form of clustering may be useful, for example, in a single stimulation source IMD in which the source is multiplexed across multiple electrodes, but intensity of stimulation delivered by particular electrodes cannot be individually controlled. In this manner, electrodes having compatible amplitude versus threshold ranges can be clustered together and driven together by the same source with the same amplitude.

In some examples, where an implantable medical device includes independent current/voltage sources for each electrode (as illustrated in and described with reference to FIG. 5), electrodes may be clustered based on similar usability ranges exclusive of particular values of lower and upper thresholds for the different usability ranges. In such examples, similar usability ranges are those ranges that have the same absolute range of stimulation intensities, but not necessarily the same lower and upper bounds. In such examples, the electrode combinations, despite having different stimulation thresholds, may be clustered because the amplitude provided to each electrode combination in a cluster may be independently controlled and may be scaled relative to one another. For example, if one electrode includes a cathodic usability range of 2-4 mA and another electrode includes a cathodic usability range of 3-5 mA, then these electrodes could be clustered and amplitude may be specified in terms of mA above the lower bound of the usability range (i.e. 0-2 mA). In one example, all or any subset of electrodes could be clustered and amplitude may be specified as a percentage of the usability range (i.e. 0-100 percent of the range from the lower bound to the upper bound). In this way, the set of parameters could be common to all the electrodes in the cluster. In some applications, it may be advantageous to specify the amplitude on a logarithmic scale instead of a linear scale (e.g., in decibels above the lower bound or percentage of the distance from the lower bound to the upper bound on a log-log scale).

In another example, if one electrode has a paresthesia threshold of 5 mA and a upper threshold of 10 mA, and a second has thresholds of 2.5 and 5 mA respectively, then they may be clustered using independent current sources as follows. The first electrode may be set to 66% and the second electrode set to 33%. At a master or total amplitude of 7.5 mA for both the electrodes, the first electrode may receive 66% of 7.5 mA or 5 mA, which is the perception threshold for the first electrode. The second electrode may receive 33% of 7.5 mA or 2.5 mA, which is the perception threshold for the second threshold. In this way, the two electrodes can be clustered even though their absolute perception and upper thresholds are significantly different and, in fact, non-overlapping.

Figure 15:
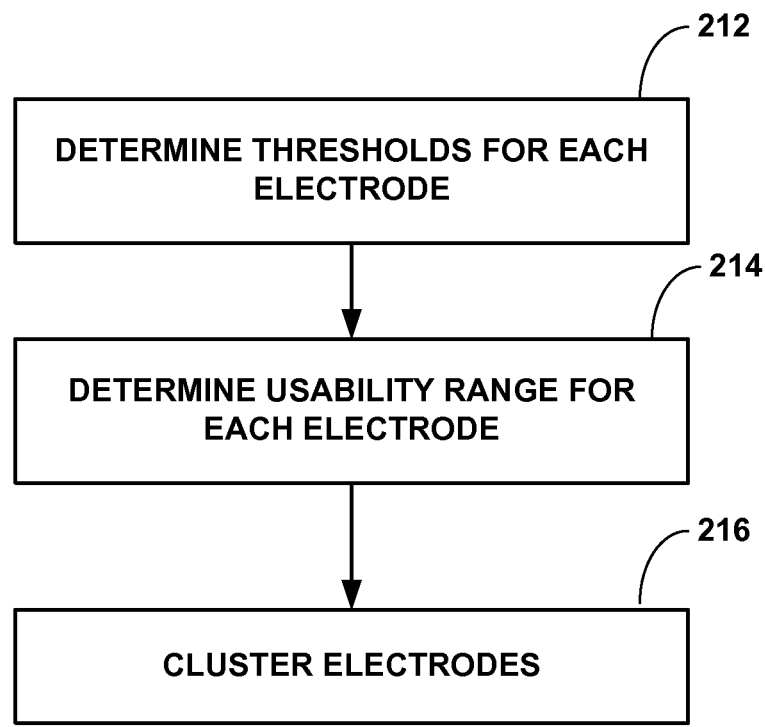
FIG. 15 is a flow diagram illustrating a method of clustering electrodes consistent with examples in this disclosure for delivery of stimulation therapy to a patient.

FIG. 15 is a flow diagram illustrating a method of clustering electrodes consistent with examples in this disclosure. The method of FIG. 15 includes determining stimulation thresholds for a number of electrodes arranged adjacent nerve tissue (212), determining usability ranges for the electrodes based on the stimulation thresholds (214), and clustering a number of the electrodes based on at least one of stimulation thresholds or usability ranges associated with the clustered electrodes (216).

In some examples, programmer 26 determines threshold(s) for each electrode (212). The determination of the thresholds may include a determination of the perception threshold according to the method discussed above with respect to FIG. 9. In some examples, a paresthesia threshold and upper threshold may also be determined for each electrode. The upper threshold may be a discomfort threshold, a pain threshold, or a muscle recruitment threshold, for example. Based on the determined threshold, a usability range for each electrode is determined (214), e.g., a usability range is calculated by processor 53 of programmer 26 for each electrode and stored in memory 55 and/or memory 52 of IMD 12. In other examples, IMD 12, using processor 50, may determine the usability range. In some examples, the usability range is from the paresthesia threshold to an upper threshold for each electrode. In some examples, the usability range is from the perception threshold to an upper threshold.

Based on the electrodes various thresholds and usability ranges, the electrodes are clustered (216) by programmer 26 or IMD 12. In some examples, the electrodes are clustered based on threshold. Electrodes or combinations of electrodes having similar threshold levels may be clustered. For example, electrodes having similar perception thresholds or paresthesia thresholds may be clustered. In some examples, electrodes are clustered based on the upper thresholds. That is, based on the highest useable stimulation intensity for a particular electrode. In some examples, the electrodes are first clustered by paresthesia threshold, and then the cluster may be pruned to electrodes within the cluster having usability ranges within a certain range. In other examples, the cluster is pruned to include electrodes with a usability range greater than a predetermined threshold. In some examples a cluster is formed around a particular electrode. In such clusters, electrodes having similar thresholds, to those of the chosen electrode are clustered with the chosen electrode. Clustering based on threshold values is often employed for stimulators that include a single stimulation source, or when the number of programs desired is greater than the number of sources available to deliver stimulation according to distinct programs. Such clustering results in electrodes being grouped together that have compatible amplitude versus threshold ranges which may be driven by the same current/voltage source.

In some examples, electrodes or electrode combinations may be clustered based on similar usability ranges. In such cases, each electrode within a cluster may be driven by an independent current/voltage source. As described in greater detail with respect to FIG. 15, in such clustering the stimulation intensity may be modified for each of the individual electrodes by an intensity factor that relates to the relative values of the thresholds. The program parameters may be modified based on the intensity factor.

Figure 16:
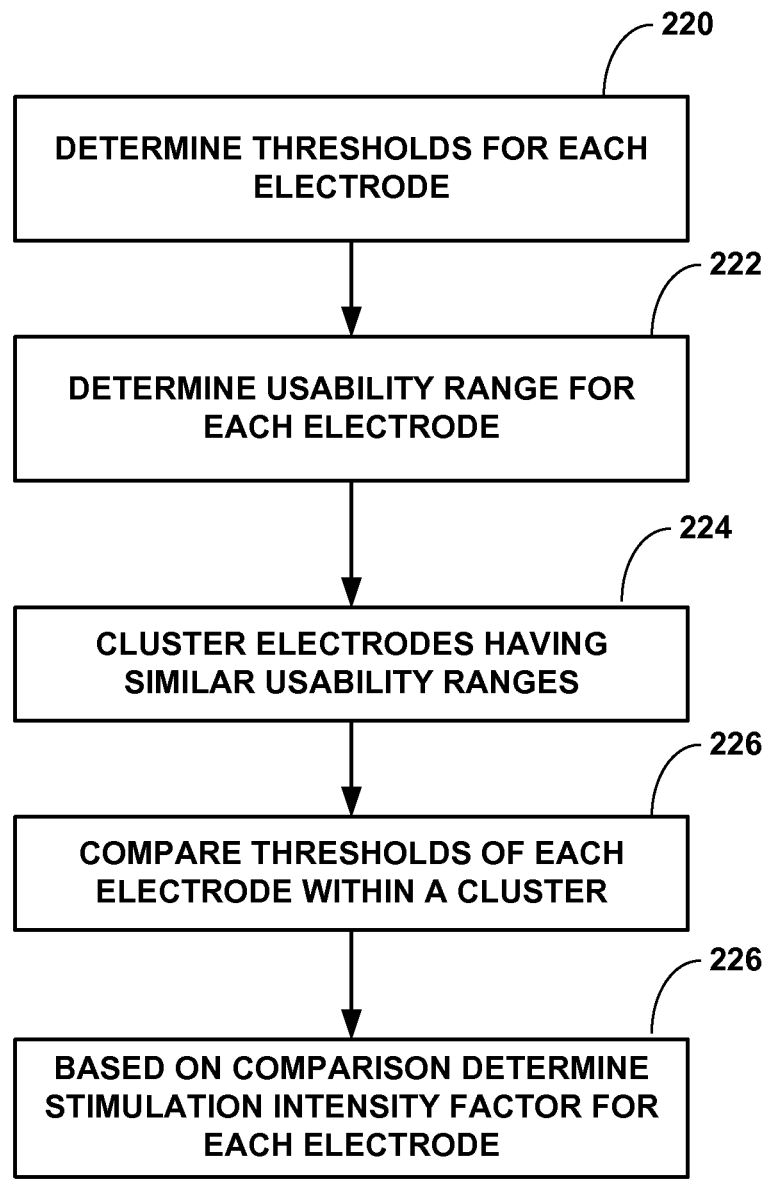
FIG. 16 is a flow diagram illustrating another method of clustering electrodes for delivery of stimulation therapy to a patient.

FIG. 16 is a flow diagram illustrating another method of clustering electrodes consistent with examples in this disclosure. The method of FIG. 16 includes determining stimulation thresholds for a number of electrodes arranged adjacent nerve tissue (220), determining usability ranges for the electrodes based on the stimulation thresholds (222), clustering a number of the electrodes including similar usability ranges (224), comparing stimulation thresholds of each electrode within the cluster (226), and based on comparison of stimulation thresholds, determine stimulation factor for each electrode in cluster (226).

In some examples, external programmer 26 determines thresholds for each electrode (220) based on stimulation intensity. Based on the determined thresholds, the external programmer 26 determines a usability range for each electrode (or electrode combination) (222). In some examples, the usability range is the range between a paresthesia threshold and an upper threshold. The upper threshold may be one of a discomfort threshold, a pain threshold, and a muscle recruitment threshold. The programmer 26 then clusters electrodes having similar usability ranges (224). That is, electrodes having usability ranges of approximately the same length. After the clustering, the programmer 26 compares the thresholds of each electrode within a cluster (226). The threshold compared may be the lower threshold of the usability range, for example the paresthesia threshold. Based on the relationship between each electrode and a standard electrode, a stimulation intensity factor for each electrode is determined (226). In some examples, the standard electrode is the electrode with the lowest paresthesia threshold. The standard electrode may have a factor of 1×, while each of the other electrodes have an intensity factor approximately equal to a multiple which will result in a threshold value equal to that of the standard electrode. For example, if the standard has a paresthesia threshold of 2, and another electrode has a paresthesia threshold of 4, then the stimulation intensity factor would be 0.5×. The stimulation intensity factor indicates the relative intensity of the stimulation signal to be provided to each electrode. The use of the stimulation intensity factor allows for modification of a program's parameters for use with electrodes having different thresholds, but similar usability ranges.

Referring again to FIG. 8, the example method also includes creating a program including a set of stimulation parameters by which stimulation may be delivered via the clustered electrodes (130). In some examples, programmer 26 creates a stimulation program. For example, processor 53 of programmer 26 may collect a selection of electrodes 48, e.g., individual or combination of electrodes selected based on nerve mapping and, in some examples, clustered together, and a set of stimulation parameters according to which stimulation generator 60 may be controlled to deliver stimulation via the electrodes. The program created may be stored in memory 55 of programmer 26 and/or memory 52 of IMD 12. In some examples, programmer 26 may create a number of stimulation programs, each program associated with a different electrode, electrode combination, or cluster of electrodes. In some examples, a clinician selects values for a number of programmable stimulation parameters in order to define the electrical stimulation therapy to be delivered to a patient according to the program being created. For example, the clinician may select a current or voltage amplitude of the stimulation, and various characteristics of the stimulation waveform that will be delivered by the electrode, electrode combination, or cluster of electrodes selected for the program. The stimulation parameters, along with an indication of which electrodes are associated with the parameters, may then be transmitted to IMD 12 via telemetry module 56 in the form of a stimulation program. In some examples, the set of parameter values may be chosen by a clinician at least in part based on the results of testing stimulation parameters described above with reference to step 126 of the example method of FIG. 8.

Under some circumstances, the effectiveness of stimulation therapy programmed and delivered to a patient may change over time. In some examples, a permanent change may occur in the relative location of the electrodes and the nerve within a patient. For example, over time, the electrodes and the lead to which they are attached may migrate within the body of the patient, thus changing the location of the nerve relative to particular electrodes. In such cases, it may be necessary to reprogram some or all of the electrodes and/or stimulation programs by which therapy is delivered to a patient. More generally, some patients may require additional programming sessions after an initial session to adjust stimulation parameters and/or electrode combinations to improve the efficacy of therapy. As such, after an initial programming session, which may be executed in accordance with the example method of FIG. 8 or other programming techniques according to this disclosure, another maintenance or reprogramming session may be conducted for a patient.

Figure 17:
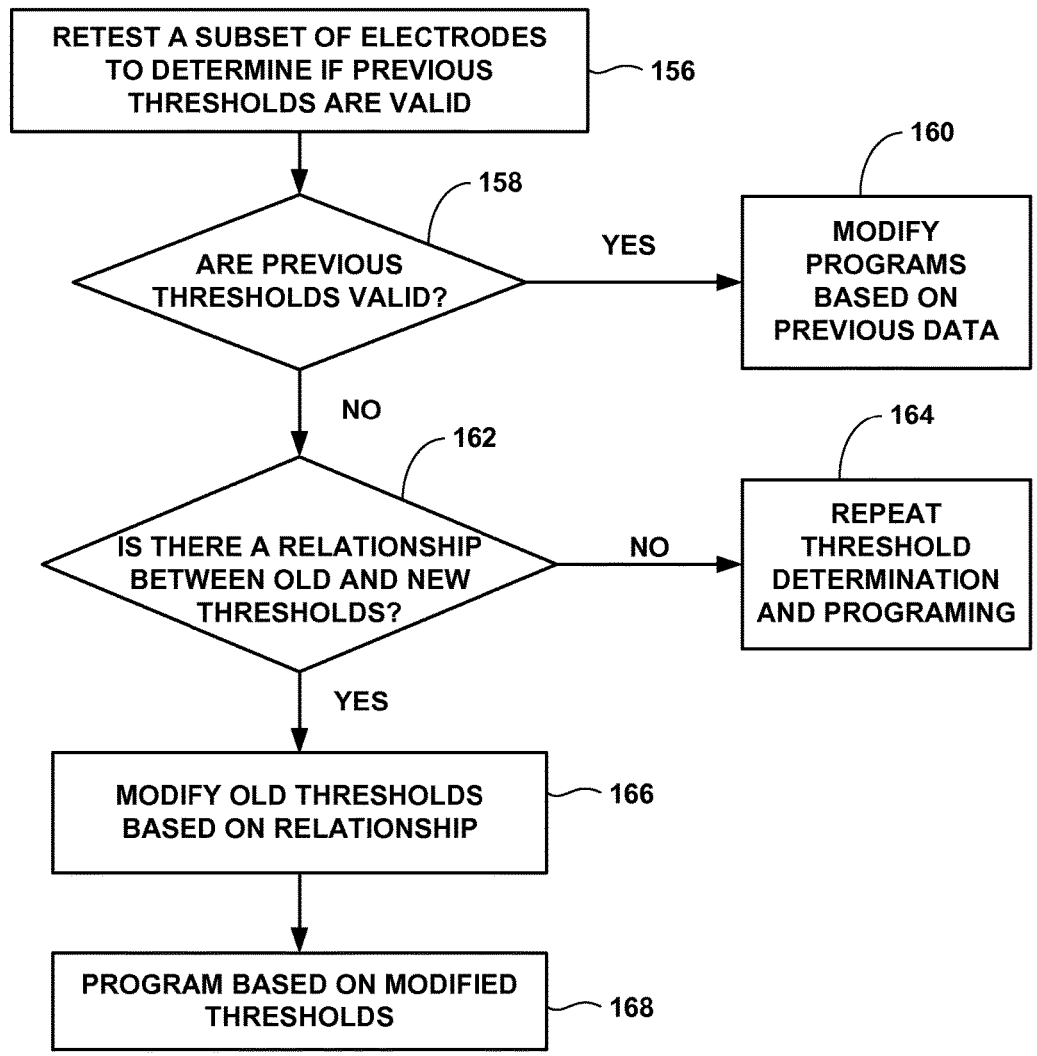
FIG. 17 is a flow diagram illustrating a method of reprogramming an implantable stimulator.

FIG. 17 is a flow diagram illustrating a method of reprogramming an IMD including retesting stimulation thresholds for a subset of previously tested electrodes (156) and determining if previously determined stimulation thresholds for the subset of electrodes are still valid (158). In the event the stimulation thresholds for the subset of electrodes are still valid, stimulation parameters and programs including a number of parameters may be modified and tested based on the previously determined stimulation thresholds (160). If, however, the previously determined stimulation thresholds for the subset of electrodes are not still valid, the method of FIG. 17 includes determining if there is a relationship between the previously determined thresholds and the new stimulation thresholds for the subset of electrodes (162). If there is no relationship between the old and new thresholds, the example method of FIG. 17 includes repeating a threshold determination for all of the electrodes and reprogramming stimulation based on the new stimulation thresholds (164). If, however, there is a relationship between the old and new thresholds, the old thresholds for the previously tested electrodes may be automatically modified based on the relationship between the old stimulation thresholds of the subset of electrodes retested and the new stimulation thresholds of the subset of electrodes (166). The example method of FIG. 17 also includes programming the IMD to deliver stimulation via the previously tested electrodes based on the modified stimulation thresholds for the electrodes (168).

In some examples according to this disclosure, a clinician may create a program or a number of programs, e.g., employing programmer 26, according to which IMD 12 may deliver stimulation therapy to patient 16. In some examples, the program is created using a method similar to the one discussed with respect to FIG. 8. In some examples, after such an initial programming session, patient 16 may have a follow up appointment to report on the continued level of efficacy of the stimulation therapy and to further improve the efficacy of the stimulation by, e.g., retesting and, in some cases, modifying the stimulation parameters and/or electrode combinations by which IMD 12 delivers stimulation to the patient. In some examples, patient 16 may visit a physician because the stimulation therapy has become ineffective or uncomfortable. A clinician, using external programmer 26 to control IMD 12, may retest a subset of electrodes previously determined to provide efficacious therapy and included in one or more stimulation programs to determine if the previous data for the subset of electrodes is still valid (156). In the example of FIG. 16, the data includes various threshold values and usability ranges for each of the subset of electrodes associated with IMD 12, e.g., a subset of electrodes 48 connected to IMD 12 via leads 14 and 15.

The values from the original, or previous, determination of thresholds for each of the subset of electrodes may be stored in memory 52 of IMD 12 and/or memory 55 of programmer 26, and after retesting, compared, by processor 50 or processor 53, to the new values. The comparison of the old thresholds to the new thresholds is used to determine if the previously determined stimulation thresholds are still valid for the subset of electrodes retested (158). In one example, the previous thresholds may be considered valid if the new thresholds are within a predetermined range of the old values. In some examples, the new thresholds may be deemed valid if they are within 5% of the previous threshold values. If the data is determined to be valid, then the clinician modifies the stimulation program(s) according to which IMD 12 delivers therapy to patient 16 based on the previously determined stimulation thresholds (160). The modifications may be based on feedback from patient 16 regarding the effectiveness of various stimulation parameters that the clinician may test to further improve the efficacy of stimulation delivered by IMD 12 to the patient.

In examples where the previous thresholds for the subset of electrodes retested are not found to be valid, programmer 26, and, in particular, processor 53 may, in one example, determines if there is a relationship between the old and new stimulation thresholds for the subset of electrodes (162). In some examples, processor 53 of programmer 26 may determine that the threshold values for each electrode have shifted a certain number of electrodes in a particular direction. This may indicate that the lead carrying the electrodes, e.g., one of leads 14 or 15 carrying some of electrodes 48A-48Q has changed position with respect to the nerve being stimulated, e.g., with respect to an occipital nerve of patient 16. In some examples, the threshold values for each electrode may have moved up or down the intensity scale. This may indicate that the electrode has moved closer to or farther away from the target nerve. If such a relationship is detected, processor 53 of programmer 26 may modify the stimulation thresholds stored in memory 52 or memory 55 associated with each of the electrodes by which IMD 12 delivers stimulation based on the identified relationship between the previously determined thresholds and the new thresholds (166) derived from the subset of electrodes retested. Processor 53 of programmer 26 may also, in some examples, alter stimulation parameters determined by the stimulation thresholds such as amplitudes, pulse widths, or patient limits. Altering such parameters automatically based on the determined relationship may save the user steps of manual manipulation and thereby make reprogramming more efficient.

In some examples, the clinician, using programmer 26, may create a new program based on the modified stimulation thresholds (168). In some examples, the new program may simply be a shift along a lead of which electrodes provide stimulation based on the parameter values of the old program. For example, in the event that processor 53 of programmer 26 determines that the threshold values for each electrode have shifted a certain number of electrodes in a particular direction, the new program may simply shift the electrode combination previously used for the old program along the lead in the indicated direction, thereby selecting a new electrode combination through which to deliver stimulation according to the same parameters previously employed. In some examples a determination may be made that the relative location of the lead and the nerve has rotated. In such examples, the stimulation vectors may be automatically rotated based on the amount of rotation detected. In some examples, the clinician may modify the parameter values in addition to shifting the electrodes which provide therapy based on the parameter values. In some examples, the new program and modified stimulation parameter values may be based on patient feedback during the session or previously recorded. For example, patient programmer 28 may store information regarding modifications to the stimulation therapy parameters patient 16 has made since the last visit to the clinician, which may be used as a basis to modify stimulation programs during the reprogramming session. The new program may be transmitted to IMD 12 via telemetry module 56 and stored in memory 52. In some examples, modifications to the program may be based on a patient's current description of symptoms. In cases where there is no evident relationship between the old and new data, programmer 26 may be employed to repeat both threshold determinations and stimulation programming (164) using, for example, the method of FIG. 8.

Techniques described in this disclosure associated with control electronics of an IMD or external device, such as an external programmer may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform various functions, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable storage media.

Various examples have been described. These and other examples are within the scope of the following claims.

The invention claimed is:

1. A method comprising:
applying electrical stimulation to a nerve of a patient via each of a plurality of implantable electrodes arranged in at least one row and at different axial positions along an axial length of a lead, the lead and the plurality of implantable electrodes having an orientation transverse to the nerve and crossing proximate to the nerve to position one or more of the plurality of implantable electrodes in proximity to the nerve, wherein each of the plurality of implantable electrodes is coupled to an implantable electrical stimulator configured to generate the electrical stimulation to deliver stimulation therapy via at least some of the plurality of implantable electrodes;
determining, respective intensity threshold levels for each of the plurality of implantable electrodes, the respective intensity threshold levels for each of the plurality of implantable electrodes including a first intensity threshold level corresponding to at least one of a perception stimulation threshold or a paresthesia stimulation threshold and a second intensity threshold level corresponding to an upper stimulation threshold of the nerve for electrical stimulation delivered by that respective electrode of the plurality of implantable electrodes, the determining comprising adjusting intensities of the electrical stimulation applied via each of the plurality of implantable electrodes to the first intensity threshold level corresponding to the at least one of the perception stimulation threshold or the paresthesia stimulation threshold and the second intensity threshold level corresponding to the upper stimulation threshold of the nerve; and
mapping a location of the nerve relative to each of the plurality of implantable electrodes based at least in part on the respective intensity threshold levels determined for each of the plurality of implantable electrodes.

2. The method of claim 1, wherein adjusting intensities comprises increasing the intensities of the electrical stimulation applied via each respective electrode of the plurality of implantable electrodes from a base level to each of the respective intensity threshold levels.

3. The method of claim 1, wherein mapping the location of the nerve relative to each of the plurality of implantable electrodes comprises mapping the location of the nerve relative to each of the plurality of implantable electrodes based on a usability range for the respective electrode of the plurality of implantable electrodes, wherein the usability range for the respective electrode of the plurality of implantable electrodes is defined as the difference between the first intensity threshold level corresponding to the at least one of the perception stimulation threshold or the paresthesia stimulation threshold and the second intensity threshold level corresponding to the upper stimulation threshold of the nerve for electrical stimulation delivered by that respective electrode of the plurality of implantable electrodes.

4. The method of claim 1, wherein mapping the location of the nerve relative to each of the plurality of implantable electrodes comprises mapping a relative location derived in both an X and a Y direction between the nerve and the respective electrode of the plurality of implantable electrodes.

5. The method of claim 1, wherein mapping the location of the nerve relative to the each of the plurality of implantable electrodes comprises mapping a relative orientation between the nerve and the respective electrode of the plurality of implantable electrodes.

6. The method of claim 1, further comprising automatically selecting one or more of the plurality of implantable electrodes to apply chronic electrical stimulation to a tissue adjacent the nerve based on the location of the nerve relative to the one or more of the plurality of implantable electrodes.

7. The method of claim 1, further comprising automatically selecting one or more of the plurality of implantable electrodes to apply chronic electrical stimulation to a tissue adjacent the nerve based on at least one of the first intensity threshold level corresponding to the at least one of the perception stimulation threshold or the paresthesia stimulation threshold and the second intensity threshold level corresponding to the upper stimulation threshold for each of the plurality of implantable electrodes.

8. The method of claim 1, further comprising: displaying a graphical representation of the location of the nerve relative to the electrodes.

9. The method of claim 1, wherein the upper stimulation threshold corresponds to a pain threshold or a discomfort threshold.

10. The method of claim 6, further comprising: delivering the chronic electrical stimulation to the tissue adjacent the nerve based on the selection of the one or more of the plurality of implantable electrodes.

11. The method of claim 7, further comprising: delivering the chronic electrical stimulation to the tissue adjacent the nerve based on the selection of the one or more of the plurality of implantable electrodes.

12. The method of claim 1, wherein mapping the location of the nerve further comprises determining that an electrode of the plurality of implantable electrodes with a lowest respective first intensity threshold level corresponding to the at least one of the perception stimulation threshold or the paresthesia stimulation threshold is the electrode of the plurality of implantable electrodes that is closest to the nerve.

13. The method of claim 1, wherein the at least one row of the plurality of implantable electrodes comprises only a single row extending along the axial length of the lead.

14. The method of claim 1, wherein the at least one row of the plurality of implantable electrodes comprises a plurality of rows arranged on an implantable paddle lead.

15. A system comprising:
an implantable lead;
a plurality of implantable electrodes arranged in at least one row and at different axial positions along an axial length of the implantable lead, the lead and the plurality of implantable electrodes having an orientation transverse to a nerve of a patient and crossing proximate to the nerve to position one or more of the plurality of implantable electrodes in proximity to the nerve;
an implantable electrical stimulator connected to the plurality of implantable electrodes and configured to generate electrical stimulation to deliver stimulation therapy via at least some of the plurality of implantable electrodes; and
a processor configured to control the implantable electrical stimulator to:
apply electrical stimulation to the nerve of the patient via each of the plurality of implantable electrodes;
determine, respective intensity threshold levels for each of the plurality of implantable electrodes, the respective intensity threshold levels for each of the plurality of implantable electrodes including a first intensity threshold level corresponding to at least one of a perception stimulation threshold or a paresthesia stimulation threshold and a second intensity threshold level corresponding to an upper stimulation threshold of the nerve for electrical stimulation delivered by that respective electrode of the plurality of implantable electrodes, the determination comprising adjusting intensities of the electrical stimulation applied via each of the plurality of implantable electrodes to the first intensity threshold level corresponding to the at least one of the perception stimulation threshold or the paresthesia stimulation threshold and the second intensity threshold level corresponding to an upper stimulation threshold of the nerve; and
map a location of the nerve relative to each of the plurality of implantable electrodes based at least in part on the respective intensity threshold levels determined for each of the plurality of implantable electrodes.

16. The system of claim 15, wherein the at least one row of the plurality of implantable electrodes comprises a plurality of rows arranged on an implantable paddle lead.

17. The system of claim 15, wherein the at least one row of the plurality of implantable electrodes comprises only a single row extending along the axial length of the lead.

18. The system of claim 15, wherein to adjust the intensities, the processor is configured to increase the intensities of the electrical stimulation applied via each respective electrode of the plurality of implantable electrodes from a base level to each of the respective intensity threshold levels.

19. The system of claim 15, wherein the processor is configured to map the location of the nerve relative to each of the plurality of implantable electrodes based on a usability range for the respective electrode of the plurality of implantable electrodes, wherein the usability range for each of the plurality of implantable electrodes is defined as the difference between the first intensity threshold level corresponding to the at least one of the perception stimulation threshold or the paresthesia stimulation threshold and the second intensity threshold level corresponding to the upper stimulation threshold of the nerve for electrical stimulation delivered by that respective electrode of the plurality of implantable electrodes.

20. The system of claim 15, wherein the processor is configured to map the location of the nerve relative to each of the plurality of implantable electrodes by mapping a relative location derived in both an X and a Y direction between the nerve and the respective electrode of the plurality of implantable electrodes.

21. The system of claim 15, wherein the processor is configured to map the location of the nerve relative to each of the plurality of implantable electrodes by mapping a relative orientation between the nerve and the respective electrode of the plurality of implantable electrodes.

22. The system of claim 15, wherein the processor is configured to automatically select one or more of the plurality of implantable electrodes to apply chronic electrical stimulation to a tissue adjacent the nerve based on the location of the nerve relative to the one or more of the plurality of implantable electrodes.

23. The system of claim 15, wherein the processor is configured to control a graphical user interface to: display a graphical representation of the location of the nerve relative to the electrodes.

24. The system of claim 15, wherein the upper stimulation threshold corresponds to a pain threshold or a discomfort threshold.

25. The system of claim 22, wherein the processor is configured to: deliver the chronic electrical stimulation to the tissue adjacent the nerve based on the selection of the one or more of the plurality of implantable electrodes.

26. The system of claim 15, wherein the processor is configured to map the location of the nerve relative to each of the plurality of implantable electrodes by determining that an electrode of the plurality of implantable electrodes with a lowest respective first intensity threshold level corresponding to the at least one of the perception stimulation threshold or the paresthesia stimulation threshold is the electrode of the plurality of implantable electrodes that is closest to the nerve.

27. A computer-readable storage medium comprising instructions for causing a programmable processor to:
control an implantable electrical stimulator to apply electrical stimulation to a nerve of a patient via each of a plurality of implantable electrodes arranged in at least one row and at different axial positions along an axial length of a lead, the lead and the plurality of implantable electrodes having an orientation transverse to the nerve and crossing proximate to the nerve to position one or more of the plurality of implantable electrodes in proximity to the nerve, wherein each of the plurality of implantable electrodes is coupled to an implantable stimulation generator configured to generate the electrical stimulation to deliver stimulation therapy via at least some of the plurality of implantable electrodes;
determine, respective intensity threshold levels for each of the plurality of implantable electrodes, the respective intensity threshold levels for each of the plurality of implantable electrodes including a first intensity threshold level corresponding to at least one of a perception stimulation threshold or a paresthesia stimulation threshold and a second intensity threshold level corresponding to an upper stimulation threshold of the nerve for electrical stimulation delivered by that respective electrode of the plurality of implantable electrodes, the determination comprising adjusting intensities of the electrical stimulation applied via each of the plurality of implantable electrodes to the first intensity threshold level corresponding to the at least one of the perception stimulation threshold or the paresthesia stimulation threshold and the second intensity threshold level corresponding to the upper stimulation threshold of the nerve; and map a location of the nerve relative to each of the plurality of implantable electrodes based at least in part on the respective intensity threshold levels determined for each of the plurality of implantable electrodes.

* * * * *